United States Patent [19]

Miyawaki et al.

[11] Patent Number: 4,860,760
[45] Date of Patent: Aug. 29, 1989

[54] ELECTRONIC BLOOD PRESSURE METER INCORPORATING COMPENSATION FUNCTION FOR SYSTOLIC AND DIASTOLIC BLOOD PRESSURE DETERMINATIONS

[75] Inventors: Yoshinori Miyawaki, Yawata; Kazuhiro Matumoto, Kyoto; Osamu Shirasaki, Amagasaki, all of Japan

[73] Assignees: Omron Tateisi Electronics Co.; Isao KAI, both of Kyoto, Japan

[21] Appl. No.: 49,871

[22] Filed: May 14, 1987

[30] Foreign Application Priority Data

May 15, 1986 [JP] Japan .................... 61-112381
May 16, 1986 [JP] Japan .................... 61-113078
May 23, 1986 [JP] Japan .................... 61-119754

[51] Int. Cl.[4] ............................ A61B 5/02; A61B 5/00
[52] U.S. Cl. .................................. 128/680; 128/681; 128/682
[58] Field of Search ............... 128/680, 681, 682, 683, 128/677; 364/416

[56] References Cited

U.S. PATENT DOCUMENTS 4,638,810  1/1987  Ramsey, III et al. ............ 128/681

FOREIGN PATENT DOCUMENTS 0154995  9/1985  European Pat. Off. .
2092309  8/1982  United Kingdom .

OTHER PUBLICATIONS

Design & Developement of a New Electronic Sphygmomanometer, Vachtsevanos et al.; *Medical & Biological Engr. & Computing* (Sep. 1985).

Primary Examiner—Leo P. Picard
Assistant Examiner—Jessica J. Harrison
Attorney, Agent, or Firm—Wegner & Bretschneider

[57] ABSTRACT

In an electronic blood pressure meter, there are included a cuff adapted to be fitted around the arm of a patient whose blood pressure is to be measured and formed with a cavity, a device for pressurizing the cavity in the cuff, a device for gradually depressurizing the cavity in the cuff, a device for sensing the pressure in the cavity in the cuff and for producing an output signal representative thereof, a device for detecting a pulse wave component in the output signal produced by the sensing device, a device for determining the amplitude of the thus detected pulse wave component, a device for determining values for systolic blood pressure and diastolic blood pressure according to the thus determined amplitude of the pulse wave component and according to the output signal produced by the pressure sensing device, and a device for performing compensation relating to the values for systolic blood pressure and diastolic blood pressure. Optionally, the means for performing compensation relating to the values for systolic blood pressure and diastolic blood pressure may include a device for determining a compensation parameter and a device for compensating the amplitude of the pulse wave component as determined by the determining device therefor, according to the compensation parameter; or it may include a device for performing an arithmetic compensation operation on at least one of the values for systolic blood pressure and diastolic blood pressure, as determined by the determining device therefor.

8 Claims, 11 Drawing Sheets

ELECTRONIC BLOOD PRESSURE METER INCORPORATING COMPENSATION FUNCTION FOR SYSTOLIC AND DIASTOLIC BLOOD PRESSURE DETERMINATIONS

BACKGROUND OF THE INVENTION

The present invention relates to an electronic blood pressure meter, and more particularly relates to such an electronic blood pressure meter, the operation of which is, particularly, based upon the oscillation method.

In the prior art, there have been proposed various types of electronic blood pressure meter. Conventionally, a known type of electronic blood pressure meter the operation of which is based upon the oscillation method comprises a cuff which is fitted around the arm of a patient the blood pressure of whom it is desired to measure, a pressurization pump for selectively pressurizing the air which fills a chamber of said cuff (this process will be abbreviated as "pressurizing the cuff" hereinafter), a vent valve for selectively draining said pressurized air from said chamber in said cuff (this process will be abbreviated as "depressurizing the cuff" hereinafter), a pressure sensor for sensing the pressure of said pressurized air in said chamber of said cuff (this will be abbreviated as "cuff pressure" hereinafter) and for outputting a signal (the "cuff pressure signal") representative thereof, and a micro computer or MPU (micro processor unit) for receiving the output signal of said pressure sensor and for calculating a blood pressure value or values according thereto.

Now, the action of such a typical or conventional electronic blood pressure meter will be described in more detail with reference to FIGS. 1(a) through 1(c). These figures relate to a particular typical operational episode in which, after the cuff is fitted around the arm of a patient the blood pressure of whom it is desired to measure, first the cuff is pressurized by operation of the pressurization pump to a pressure substantially greater than the systolic blood pressure of the patient, and then subsequently the cuff is depressurized by operation of the vent valve at a substantially constant rate. FIG. 1(a) shows the behavior with respect to time of the cuff pressure signal, during this operational episode, and illustrates that a pulse wave signal is seen in said cuff pressure signal; FIG. 1(b) shows the behavior with respect to time of the peak amplitudes of this pulse wave signal for each cycle thereof, during this operational episode; and FIG. 1(c) shows the behavior with respect to time of the envelope of said peak amplitudes of said pulse wave signal.

According to the results of various clinical trials, it has been confirmed that the cuff pressure corresponding to the time point, denoted in FIGS. 1(a) and 1(c) as "M", at which the amplitude (denoted as "Ap") of the pulse wave signal reaches its maximum value, denoted in FIG. 1(c) as "Apmax", is a cuff pressure value suitably representative of the average blood pressure of the patient. And, further, according to the results of these clinical trials, it has moreover been confirmed that the cuff pressure corresponding to the time point, denoted in FIGS. 1(a) and 1(c) as "S", at which the amplitude Ap of the pulse wave signal reaches approximately 50% of its maximum value Apmax during increase of said pulse wave signal amplitude with time in the illustrated type of operational episode, i.e. to the left of the point M in FIGS. 1(a) through 1(c), is a cuff pressure value suitably representative of the systolic blood pressure (hereinafter denoted as "SYS") of the patient. And, further, again according to the results of these clinical trials, it has yet moreover been confirmed that the cuff pressure corresponding to the time point, denoted in FIGS. 1(a) and 1(c) as "D", at which the amplitude Ap of the pulse wave signal reaches approximately 70% of its maximum value Apmax during decrease of said pulse wave signal amplitude with time in the illustrated type of operational episode, i.e. to the right of the point M in FIGS. 1(a) through 1(c), is a cuff pressure value suitably representative of the diastolic blood pressure (hereinafter denoted as "DIA") of the patient.

There is however a problem with such an electronic blood pressure meter, in that, the more obese is the patient whose blood pressure is being measured, the flatter is the envelope of the amplitude values of the pulse wave signal, in other words the less are the changes in the amplitude of the pulse wave signal. This is thought to be because an obese patient has a relatively thick layer of fatty tissue under his or her skin, and the pulse wave, which is produced by changes in the volume of the artery or arteries which are obstructed by the constricting action of the cuff, is attenuated by this thick layer of fatty tissue before being transmitted to the cuff.

Now, on the other hand, it is the case that, when the cuff is wrapped around the arm of the patient and is pressurized, a pulse wave signal of a substantially constant amplitude, the so called background pulse wave signal, can always be observed as background to the above described varying pulse wave signal. This background pulse wave signal is generated by a background pulse wave caused by the blood flow in the artery or arteries which is or are obstructed by the constricting action of the cuff, or by minor volume change in the portion or portions of said artery or arteries which is or are closer to the heart of the patient than the portion or portions thereof which is or are being obstructed by the constricting action of the cuff; and said background pulse wave is then transmitted to the cuff and is manifested as a background component to the pulse wave signal which is sensed in the pressure in said cuff by the pressure sensor. And, according to the results of various researches which have been carried out in hospital conditions as well as others by the present inventors, it has been established that the amplitude of this background pulse wave signal is substantially constant irrespective of the actual value of the cuff pressure, and further that the amplitude of this background pulse wave signal does not vary much between one individual and another, whether said individual be obese or otherwise.

In FIG. 1(c) there is shown a case in which said background pulse wave signal has an amplitude denoted as "Ab". In this case, therefore, the true maximum amplitude value of the variable portion of the pulse wave signal, denoted as "Apmg", is equal to the observed maximum amplitude value Apmax of said pulse wave signal, minus this amplitude value Ab of the background pulse wave signal. Now, if the patient is not obese, the maximum observed pulse wave signal amplitude value Apmax is very much greater than the background pulse wave signal amplitude value Ab, and thus the influence from the background pulse wave signal can in practice be neglected. However, if on the other hand the patient is in fact obese, then the maximum observed pulse wave signal amplitude value Apmax is not so very much greater than that the influence of said background pulse wave signal amplitude value Ab that the influence from said background pulse wave signal can be neglected in practice, and problems can arise.

This matter will now be further expatiated upon with reference to FIG. 1(c). The true values for the systolic blood pressure of the patient and the diastolic blood pressure of the patient are obtained, in fact, by calculating as described above based upon the amplitude of the varying portion of the pulse wave signal, in other words based upon the true pulse wave signal amplitude. Thus, considering this true pulse wave signal amplitude which is obtained by subtracting the background pulse wave signal amplitude from the observed pulse wave signal amplitude, as shown in FIG. 1(c) the time point, denoted as "Sg", at which the true pulse wave signal amplitude reaches approximately 50% of its maximum value Apmg during increase of said true pulse wave signal amplitude with time in the illustrated type of operational episode, i.e. to the left of the point M in FIGS. 1(a) through 1(c), is a time value the cuff pressure at which is truly and accurately representative of the true systolic blood pressure (hereinafter denoted as "SYSg") of the patient. And, similarly, the time point, denoted as "Dg", at which the true pulse wave signal amplitude reaches approximately 70% of its maximum value Apmg during decrease of said true pulse wave signal amplitude with time in the illustrated type of operational episode, i.e. to the right of the point M in FIGS. 1(a) through 1(c), is a time value the cuff pressure at which is truly and accurately representative of the true diastolic blood pressure (hereinafter denoted as "DIAg") of the patient. However, the measured cuff pressure Pc (see FIG. 1(a)) at the time point S derived according to the prior art as first described above and taken as the systolic blood pressure value SYS of the patient, is substantially higher than this true systolic blood pressure value SYSg of the patient. Similarly, the measured cuff pressure Pc (see FIG. 1(a)) at the time point D derived according to the prior art as first described above and taken as the diastolic blood pressure value DIA of the patient, is substantially lower than this true diastolic blood pressure value DIAg of the patient.

These problems are exacerbated, the greater is the value of the background pulse wave amplitude Ab. Thus, if the patient is obese, a large error in measurement may occur, and further the reproducibility of the blood pressure value measurement tends to be deteriorated. In FIGS. 1(b) and 1(c), the broken lines show the pulse wave amplitude values Ap determined in another similar episode of blood pressure measurement under the same or similar conditions. The time points S' and D' are determined by the same method, in this second blood pressure measurement episode, but with regard to the broken line pulse wave amplitude values, as were the time points S and D in the first blood pressure measurement episode, with regard to the solid line pulse wave amplitude values; and it will be seen that these time points S, S' and D, D' are substantially different from one another. Further, in FIG. 1(a), the thus determined systolic blood pressure value SYS' and the thus determined diastolic blood pressure value DIA' corresponding to these time points S' and D' are also shown; and it will be seen that the systolic blood pressure values SYS and SYS', and the diastolic blood pressure values DIA and DIA', are substantially different from one another. Thus a poor accuracy and repeatability of blood pressure measurement are manifested, according to prior art methods as described above.

The more obese is the patient, the more troublesome do the above outlined problems become, and the flatter becomes the envelope of the pulse wave signal amplitude values Ap. Finally, in the case of a quite obese patient, as suggested in the exemplary case of FIG. 1(d), at no point does said pulse wave signal amplitude drop as low as 50% of its maximum amplitude Apmax, and the point S cannot be determined. In an even worse case, at no point would the pulse wave signal amplitude drop as low even as 70% of its maximum amplitude Apmax, and the point D would also become unable to be determined.

Further, another problem is liable to occur with regard to the use of a conventional type of electronic blood pressure meter, which will now be explained with reference to FIGS. 7(a) and 7(b), which relate to the prior art. Namely, it is possible for consistent, i.e. systematic, errors to be generated with respect to accurate blood pressure values as measured by the stethoscopic method.

FIG. 7(a) is a graph showing the correlation between the systolic blood pressure Saus (in mmHg) measured for a patient by using the stethoscopic method, and the systolic blood pressure Sosc (in mmHg) measured for the same patient by using such a conventional type of electronic blood pressure meter which operates according to the oscillation method. The threshold value for the pulse wave amplitude for determining the systolic blood pressure Sosc of the patient, in this exemplary case, was 60% of the maximum pulse wave amplitude. In this exemplary case, the measured systolic blood pressure Sosc tends to be relatively lower for a patient with a relatively high blood pressure and tends to be relatively higher for a patient with a relatively low blood pressure. The points plotted in FIG. 7(a) fall onto the line L's, which is a linear approximation of the correlation between these two systolic blood pressure values Sosc and Saus. This line L's can be expressed by the following linear equation:

$$Sosc = as\ Saus + bs \qquad (a)$$

The actual values of as and bs were determined, in a typical exemplary case, to be 0.91 (with no dimension) and 11.2 mmHg.

Similarly, FIG. 7(b) is a graph showing the correlation between the diastolic blood pressure Daus (in mmHg) measured for a patient by using the stethoscopic method, and the diastolic blood pressure Dosc (in mmHg) measured for the same patient by using such a conventional type of electronic blood pressure meter which operates according to the oscillation method. The threshold value for the pulse wave amplitude for determining the diastolic blood pressure Dosc of the patient, in this exemplary case, was 70% of the maximum pulse wave amplitude. In this exemplary case, the measured diastolic blood pressure Dosc again tends to be relatively lower for a patient with a relatively high blood pressure and tends to be relatively higher for a patient with a relatively low blood pressure. The points plotted in FIG. 7(b) fall onto the line L'd, which is a linear approximation of the correlation between these two diastolic blood pressure values Dosc and Daus. This line L'd can be expressed by the following linear equation:

$$Dosc = ad\ Daus + bd \qquad (b)$$

The actual values of ad and bd were determined, in a typical exemplary case, to be 0.91 (with no dimension) and 7.5 mmHg.

In the above description, the correlations between the systolic blood pressure values Sosc and Saus, and between the diastolic blood pressure values Dosc and Daus, were expressed for convenience by linear equations, but in the general case it would be more accurate to express these correlations by quadratic or higher order equations. Generally, these correlations between the systolic blood presure values Sosc and Saus, and between the diastolic blood pressure values Dosc and Daus, can be expressed in the following forms:

$$Sosc = fs(Saus) \tag{c}$$

and:

$$Dosc = fd(Daus) \tag{d}$$

and this provides an even more troublesome problem, in the general case.

SUMMARY OF THE INVENTION

The inventors of the present invention have considered the various problems detailed above.

Accordingly, it is the primary object of the present invention to provide an electronic blood pressure meter, which avoids the problems detailed above.

It is a further object of the present invention to provide such an electronic blood pressure meter, which can reliably measure the blood pressure of a patient, even when said patient is obese.

It is a further object of the present invention to provide such an electronic blood pressure meter, which has a high accuracy of blood pressure measurement.

It is a further object of the present invention to provide such an electronic blood pressure meter, which has a high repeatability and reproducibility of blood pressure measurement.

It is a further object of the present invention to provide such an electronic blood pressure meter, which is not prone to providing an indicated blood pressure value which is inaccurate.

It is a further object of the present invention to provide such an electronic blood pressure meter, which is not prone to providing an indicated systolic blood pressure value which is substantially too high.

It is a further object of the present invention to provide such an electronic blood pressure meter, which is not prone to providing an indicated diastolic blood pressure value which is substantially too low.

It is a further object of the present invention to provide such an electronic blood pressure meter, which eliminates the errors inherent in the oscillation method.

It is a further object of the present invention to provide such an electronic blood pressure meter, which can measure the blood pressure of a patient with good accuracy, no matter whether said patient has a high or a low blood pressure.

According to the most general aspect of the present invention, these and other objects are attained by an electronic blood pressure meter, comprising: (a) a cuff adapted to be fitted around the arm of a patient whose blood pressure is to be measured, and formed with a cavity; (b) a means for pressurizing said cavity in said cuff; (c) a means for gradually depressurizing said cavity in said cuff; (d) a means for sensing the pressure in said cavity in said cuff, and for producing an output signal representative thereof; (e) a means for detecting a pulse wave component in said output signal produced by said sensing means; (f) a means for determining the amplitude of said thus detected pulse wave component; (g) a means for determining values for systolic blood pressure and diastolic blood pressure, according to the thus determined amplitude of said pulse wave component and according to the output signal produced by said pressure sensing means; and: (h) a means for performing compensation relating to said values for systolic blood pressure and diastolic blood pressure.

According to such an electronic blood pressure meter as specified above, since the systolic blood pressure and the diastolic blood pressure are compensated, the problems outlined above with regard to the prior art are avoided.

According to a particular specialization of the present invention, the above and other objects may more particularly be accomplished by such an electronic blood pressure meter as specified above, wherein said means for performing compensation relating to said values for systolic blood pressure and diastolic blood pressure comprises: a means for determining a compensation parameter; and: a means for compensating the amplitude of said pulse wave component as determined by said determining means therefore, according to said compensation parameter. Thus, it is possible to remove the error due to the background pulse wave, prevalent in the prior art as outlined above, from the final results. Optionally, said compensation parameter determining means may determine said compensation parameter according to the maximum value of said amplitude of said pulse wave component as determined by said determining means therefor, and said means for compensating the amplitude of said pulse wave component may do so by subtracting said compensaton parameter therefrom. In this case, the reproducibility of measurement may be enhanced, by the compensation parameter (which may include one or more predetermined or constant parameter) reflecting the influence of the background pulse wave upon the measurement results, and compensating for such influence. In this case, even when the patient is obese, even highly obese, the pulse wave amplitude value corresponding to a certain determinate fraction of the maximum amplitude of said pulse wave can always be reliably and definitely extracted, and the systolic and diastolic blood pressures of the patient can be reliably measured without any risk of failure. Or said compensation parameter determining means may determine said compensation parameter according to the value of said amplitude of said pulse wave component as determined by said determining means therefor in a circumstance in which the pressure in said cuff is outside the pressure range of blood pressure measurement, and said means for compensating the amplitude of said pulse wave component may do so by subtracting said compensation parameter therefrom. In this case, said influence of said background pulse wave can be reliably determined. The circumstance in which the pressure in said cuff is outside the range of blood pressure measurement may be when said pressure in said cuff is below the pressure range of blood pressure measurement, or alternatively may be when said pressure in said cuff is above the pressure range of blood pressure measurement.

According to an alternative-particular-specialization of the present invention, the above and other objects may more particularly be accomplished by such an electronic blood pressure meter as first specified above, wherein said means for performing compensation relating to said values for systolic blood pressure and diastolic blood pressure comprises a means for performing an arithmetic compensation operation on at least one of said values for systolic blood pressure and diastolic blood pressure, as determined by said determining means therefor. In this case, the arithmetic compensation operation for the systolic blood pressure should be according to an equation obtained by solving the previous equation (c) mentioned above for the systolic blood pressure Saus as determined by the stethoscopic method in terms of the systolic blood pressure Sosc as determined by the oscillation method, and similarly the arithmetic compensation operation for the diastolic blood pressure should be according to an equation obtained by solving the previous equation (d) mentioned above for the diastolic blood pressure Daus as determined by the stethoscopic method in terms of the diastolic blood pressure Dosc as determined by the oscillation method. In many cases, these arithmetic compensation operations may be linear operations. Thereby, it is possible to obtain reliable measurement both of the systolic blood pressure of the patient and of the diastolic blood pressure of the patient, whether these blood pressures be high or low, without the occurrence of any systematic deviations from the blood pressure values obtained by the stethoscopic method.

BRIEF DESCRIPTION OF THE DRAWINGS

The present invention will now be described with respect to the preferred embodiments thereof, and with reference to the illustrative drawings appended hereto, which however are provided for the purposes of explanation and exemplification only, and are not intended to be limitative of the scope of the present invention in any way, since this scope is to be delimited solely by the accompanying claims. With relation to the figures, spatial terms are to be understood as referring only to the orientation on the drawing paper of the illustrations of the relevant parts, unless otherwise specified; like reference numerals, unless otherwise so specified, denote the same parts and spaces and so on in the various figures relating to one preferred embodiment, and like parts and spaces and so on in figures relating to different preferred embodiments; and:

FIG. 1 shows in its FIG. 1(d) the behavior with respect to time of the envelope of said peak amplitudes of said pulse wave signal, in a more extreme case of patient obesity;

DESCRIPTION OF THE PREFERRED EMBODIMENTS

The present invention will now be described with reference to the preferred embodiments thereof, and with reference to the figures.

The First Preferred Embodiment

FIGS. 2 through 5 relate to the first preferred embodiment of the electronic blood pressure meter of the present invention.

Basic Operation

Figure 2A:
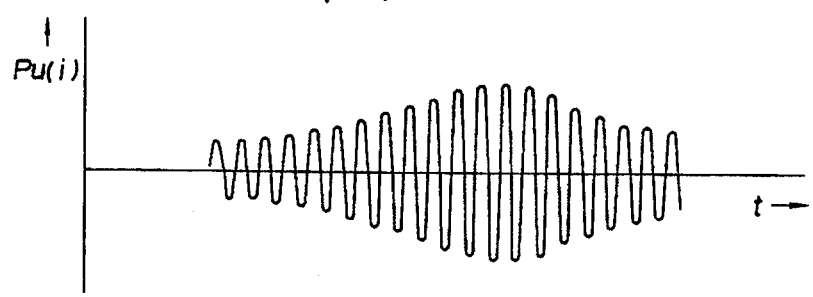
FIG. 2 is a similar series of time charts to FIG. 1, and shows in its FIGS. 2(a) through 2(c) respectively, for a particular operational episode of an embodiment of the electronic blood pressure meter of the present invention, a series of data for a pulse wave component value Pu(i) which is indicated by an envelope thereof because the sampling frequency is high, a series of data for a pulse wave amplitude value Ap(n) which are computed from the FIG. 2(a) series of data for the pulse wave component value Pu(i), and a series of data for a background compensated pulse wave amplitude value A'p(n) obtained by subtracting a background pulse wave amplitude value Ab from the data for the pulse wave amplitude value Ap(n)
Figure 2B:
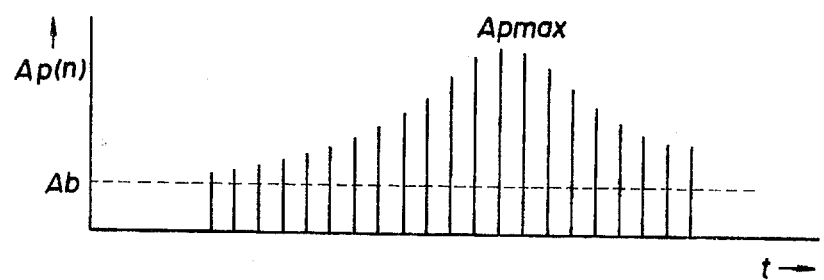

First, with reference to FIGS. 2(a) through 2(c), an explanation will be given of the basic principle of operation of this first preferred embodiment of the electronic blood pressure meter of the present invention. FIG. 2(a) shows a series of data for the pulse wave component value PU(i), which is indicated by an envelope thereof because the sampling frequency is high. FIG. 2(b) shows a series of data for the pulse wave amplitude value Ap(n), which are computed from the FIG. 2(a) series of data for the pulse wave component value Pu(i). In this FIG. 2(b), the maximum value of the series of data for the pulse wave amplitude value Ap(n) is designated as "Apmax", and the background pulse wave amplitude value in this case is designated as "Ab". In the first preferred embodiment of the electronic blood pressure meter of the present invention, the blood pressure values are obtained from this maximum pulse wave amplitude value Apmax, using this value of Ab as a compensation parameter. And in FIG. 2(c) there is shown a series of data for the backgroiund compensated pulse wave amplitude value A'p(n), obtained by subtracting the background pulse wave amplitude value Ab from the data for the pulse wave amplitude value Ap(n). As will be seen from the following, this data for the background compensated pulse wave amplitude value A'p(n) is free from the influence of the background pulse wave, and, when procedures are based upon such data for the background compensated pulse wave amplitude value A'p(n), accurate blood pressure determination is possible.

Figure 1A:
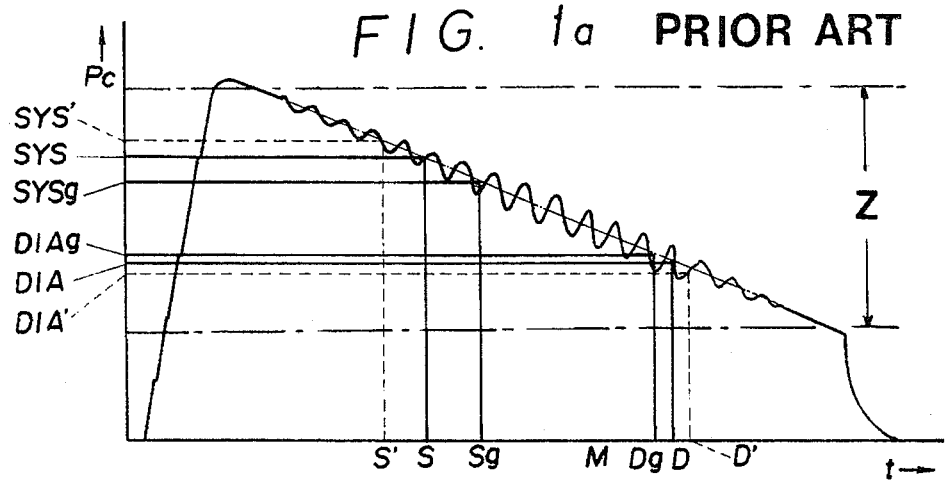
FIG. 1 is a series of time charts relating to the prior art, and shows, for a particular pair of operational episodes of a prior art electronic blood pressure meter, in its FIGS. 1(a) through 1(c) respectively, the behavior with respect to time of the cuff pressure signal, the behavior with respect to time of the peak amplitudes of this pulse wave signal for each cycle thereof, and the behavior with respect to time of the envelope of said peak amplitudes of said pulse wave signal; and further this
Figure 1B:
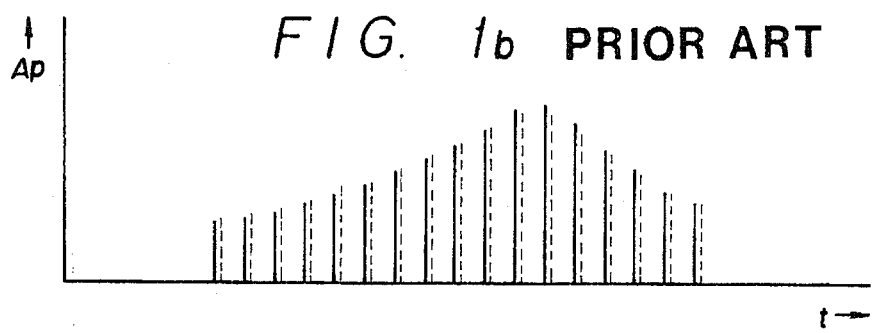
Figure 1C:
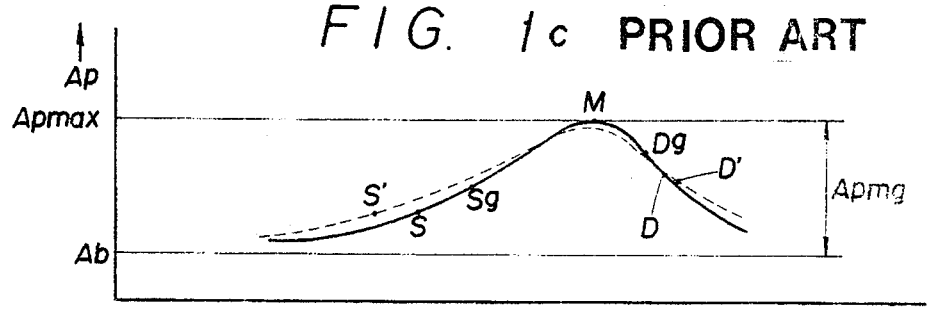
Figure 1D:
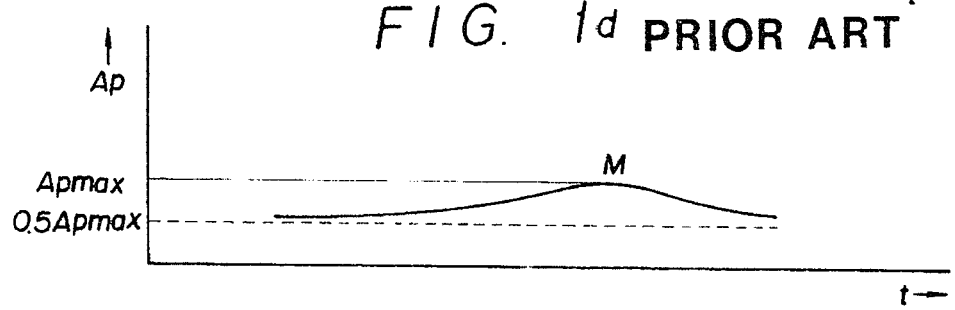
Figure 2C:
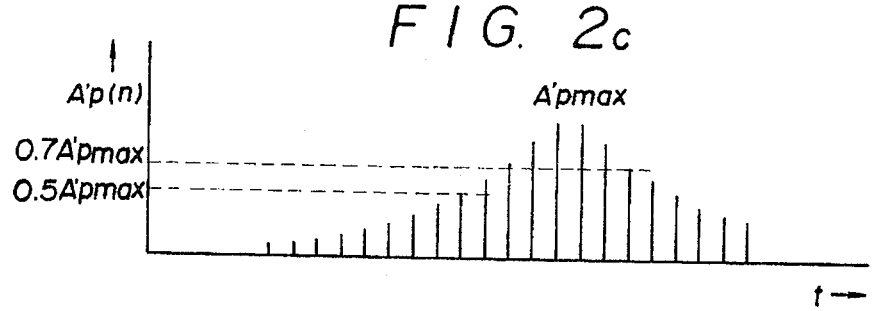

According to this first preferred embodiment of the electronic blood pressure meter of the present invention, a time point in the region of increasing pulse wave amplitude with time (to the left of the maximum value point thereof in FIGS. 2(a) through 2(c)) and at which the background compensated pulse wave amplitude value A'p(n) is closest to 50% of the maximum compensated pulse wave signal amplitude value Ap'max is designated as the time point S, and the cuff pressure Pc corresponding thereto is determined as being the systolic blood pressure of the patient. Similarly, a time point in the region of decreasing pulse wave amplitude with time (to the right of the maximum value point thereof in FIGS. 2(a) through 2(c)) and at which the background compensated pulse wave amplitude value A'p(n) is closest to 70% of said maximum compensated pulse wave signal amplitude value Ap'max is designated at the time point D, and the cuff pressure Pc corresponding thereto is determined as being the diastolic blood pressure of the patient. Thereby, even when the patient is obese, and therefore the curve of the pulse wave amplitude Ap is relatively flat, these time points S and D at which the background compensated pulse wave amplitude value A'p(n) reaches 50% and 70% of its maximum value A'p(n) respectively in its increasing with time and decreasing with time regions respectively can be easily and reliably determined, and no substantial problems of error or of indefiniteness in determining the time points S and D, such as were present in the prior art described earlier in this specification with reference to FIGS. 1(a) through 1(d) and particularly with reference to FIG. 1(d), will occur.

Construction

Figure 3:
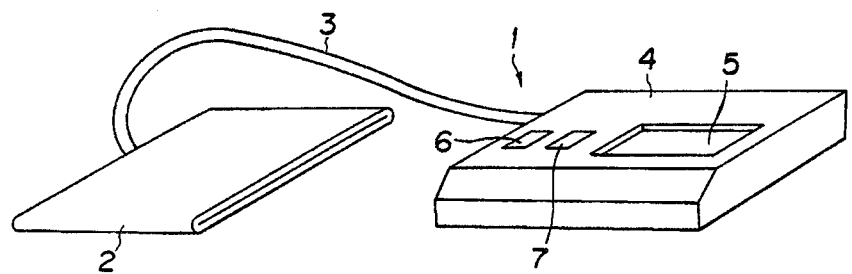
FIG. 3 is an external perspective view, and is applicable to any one of the preferred embodiments of the electronic blood pressure meter of the present invention.
Figure 4:
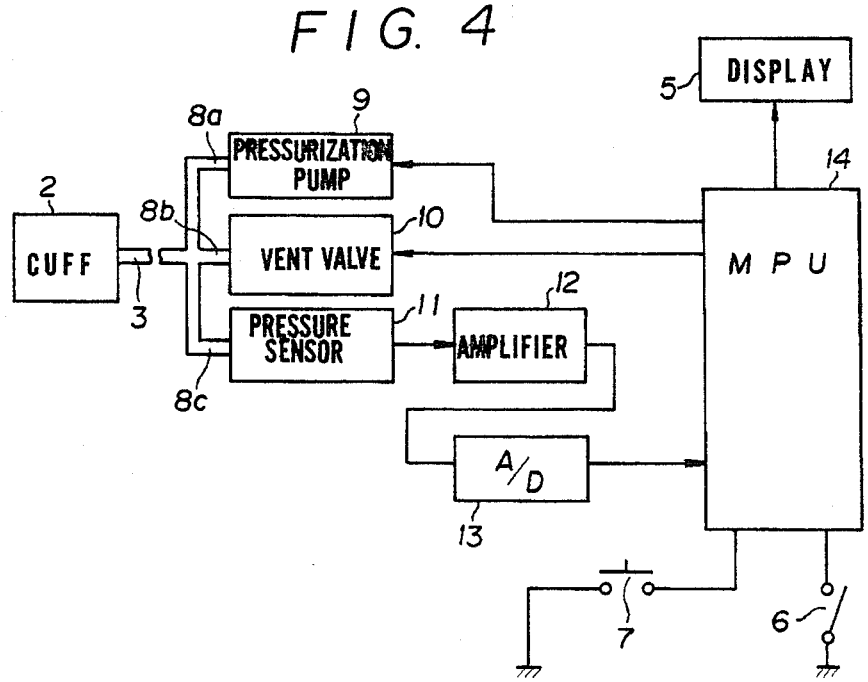
FIG. 4 is a block diagrammatical view of an air pressurization and depressurization system and pressure measurement circuit incorporated in all of said preferred embodiments of the electronic blood pressure meter of the present invention.
Figure 5A:
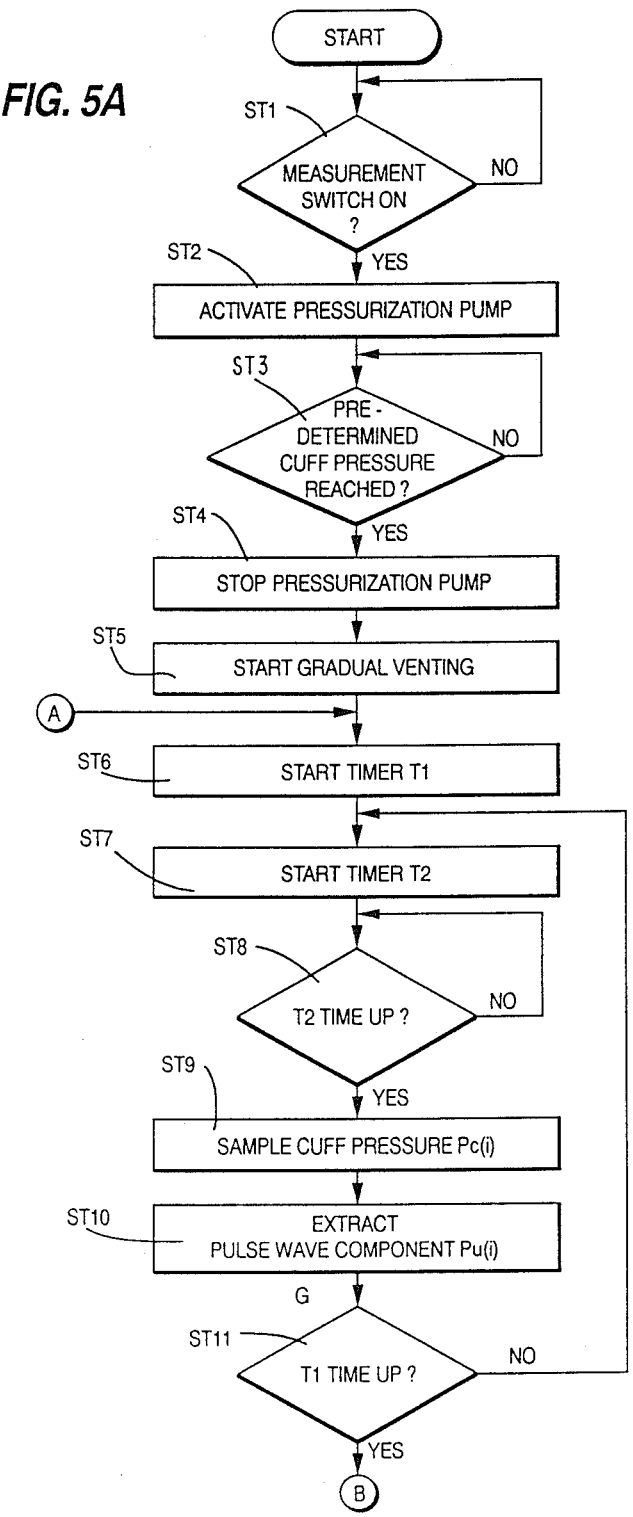
FIG. 5a and FIG. 5b are a flow chart for illustrating the operation of a portion of a program stored in and obeyed by a micro computer incorporated in said circuit of FIG. 4 in order to realize the operation of the first preferred embodiment of the electronic blood pressure meter of the present invention.
Figure 5B:
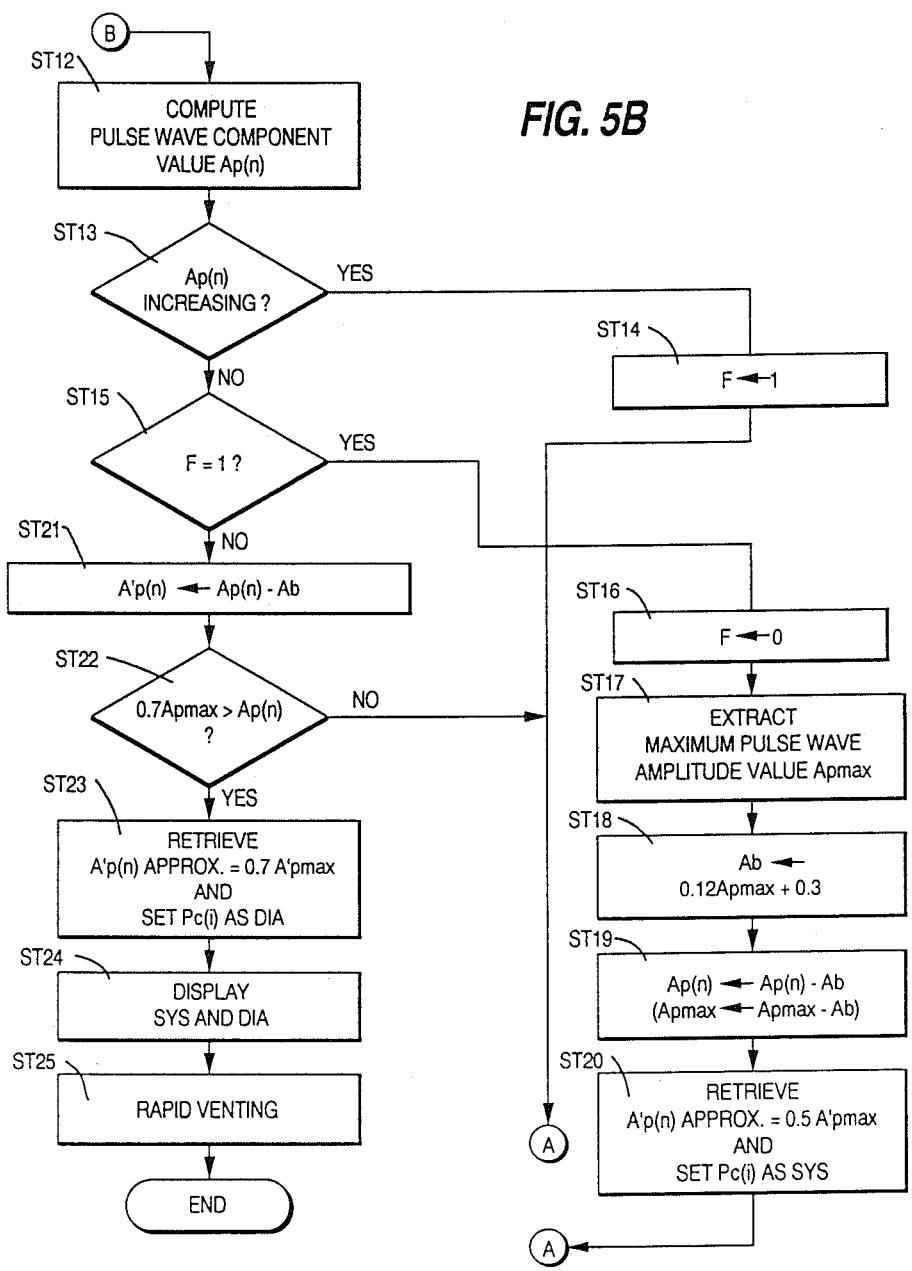

Now, to describe the concrete construction of this first preferred embodiment of the electronic blood pressure meter of the present invention, said blood pressure meter is shown in external perspective view in FIG. 3, and a block diagrammatical view of an air pressurization and depressurization system and pressure measurement circuit is shown in FIG. 4. In these figures, both of which in fact are applicable to any of the preferred embodiments of the electronic blood pressure meter of the present invention which will be described, the reference numeral 1 denotes the electronic blood pressure meter as a whole, and 2 denotes a cuff thereof, which is made as a bag of air in the shape of a band. This cuff 2 is connected to the main body 4 of the electronic blood pressure meter by way of a flexible tube 3 which is made of rubber or the like. The upper surface of said electronic blood pressure meter main body 4 is equipped with a display unit 5, which may incorporate an LCD (liquid crystal display) unit or the like, and further is equipped with a power switch 6 and a measurement switch 7.

FIG. 4 is a block diagrammatical view of an air pressurization and depressurization system and pressure measurement circuit which is incorporated in the electronic blood pressure meter main body 4. The cuff 2 is connected via the previously mentioned tube 3 and via conduits 8a, 8b, and 8c respectively to a pressurization pump 9 (which functions as a pressurization means), to a vent valve 10 (which functions as a depressurization means), and to a pressure sensor 11 (which functions as a pressure detecting means). The vent valve 10, although no hint of such structure or function is shown in the diagram, is actually structured as a double valve, and incorporates a pair of vent valves, one being a rapid vent valve and the other being a slow or gradual vent valve. And the pressure sensor 11 may be a diaphragm type pressure sensor which incorporates a strain gauge or a semiconductor pressure converter element. The pressurization pump 9 and the vent valve 10 are controlled with regard to their operation by a microcomputer or MPU which will be described hereinafter with regard to its structure and its function.

The electrical signal which is output by the pressure sensor 11 is amplified by an amplifier 12, and is converted into a digital signal by an analog/digital converter (A/D converter) 13. The microcomputer 14 receives this digitalized output signal of the pressure sensor 11, which is of a substantially constant frequency. This microcomputer 14 performs the functions of detecting the pulse wave component from this output signal of said pressure sensor 11, computing the pulse wave amplitude value, compensating this pulse wave amplitude value, determining values for the systolic blood pressure and for the diastolic blood pressure, controlling the pressurization pump 9 and the vent valve 10, and the like. And this microcomputer 14, further, is connected to the display 5, so as to show the determined blood pressure values; and said microcomputer 14 is also connected to the power switch 6 and to the measurement switch 7.

Operation

This first preferred embodiment of the electronic blood pressure meter of the present invention operates as will now be described, according to a program stored in the microcomputer 14; this program will not be particularly described herein in detail with regard to its programming steps, but only with regard to its functions and with regard to a flow chart thereof, becuase the details of the programming for implementing such functions can be easily supplemented by one of ordinary skill in the programming art relevant to the particular microcomputer which it is decided to utilize, based upon the functional disclosures set out in this specification. In this first preferred embodiment, the operation of the controller is determined according to the flow chart shown in FIG. 5a and FIG. 5b. This flow chart will now be explained.

First of all, the cuff 2 is wrapped by an operator around the upper arm of the patient whose blood pressure it is desired to measure, and then the power switch 6 is turned on.

When the power switch 6 is turned on to initiate the operation of the FIG. 5 program, the microcomputer 14 first determines, in the decision step ST1, whether or not the measurement switch 7 is turned on. If in fact the measurement switch 7 is no turned on, then the flow of control returns to this decision step ST1 again, so that the microcomputer 14 loops around and around without advancing, and the system remains in a stand by state until in fact the measurement switch 7 is turned on. On the other hand, when said measurementswitch 7 is turned on, the flow of control passes to the next step ST2.

In the step ST2, reached when the measurement switch 7 is turned on as explained abovwe, the microcomputer 14 activates the pressurization pump 9, so as to start pressurizing the cuff 2; and then the flow of control passes next to the next decision step ST3. At this point, the pressure sensor 13 is producing an electrical signal representative of the pressure Pc in the cuff 2.

Then, in this decision step ST3, a decision is made as to whether or not the cuff pressure Pc, as indicated by the output electrical signal of the pressure sensor 13, has reached a determinate threshold value. If the result of this decision is YES, so that the cuff pressure Pc has in fact reached this determinate threshold value, then the flow of control passes next to step ST4; but, if the result of this decision is NO, so that the cuff pressure Pc has ot yet in fact reached this determinate threshold value, then the flow of control passes next to this decision step ST3 again, so as to loop around until the cuff pressure Pc does reach the determinate threshold value.

In the next step ST4, the microcomputer 14 stops the operation of the pressurization pump 9, and then the flow of control passes next to the step ST5. And, in this next step ST5, the microcomputer 14 actuates the vent valve 10 so as to start gradually venting the cuff 2, i.e. so as to start gradually lowering the cuff pressure, and then the flow of control passes next to step ST6.

In this next step ST6, which also is the step back to which the flow of control returns in a large loop after the step ST14 and also after the step ST20 to be described later, the microcomputer 14 starts the counting process of a first timer, designated as T1. This timer T1 is for determining the frequency of computing the pulse wave amplitude value Ap(n) from the pulse wave component, and its timed value is normally set to be between about 1 second and about 2 seconds. And then the flow of control passes next to the step ST7.

In this next step ST7, which also is the step back to which the flow of control returns in a smaller loop after a NO decision in the decision step ST11 to be described later, the microcomputer 14 starts the counting process of a second timer, designated as T2. This timer T2 is for determining the sampling frequency of the microcomputer 14 when it takes in a value representative of the cuff pressure from the A/D converter 13, and its timed value is normally set to be between about 10 ms and about 50 ms. And then the flow of control passes next to the decision step ST8.

In this decision step ST8, a decision is made as to whether or not the timed value of the second timer T2 is up. If the result of this decision is YES, so that in fact the second timer T2 has concluded its timing and has reached its timed value, thus indicating that the time represented by the timed value of the second timer T2 has elapsed since the step ST7 above was performed, then the flow of control passes next to the step ST9; but, if the result of this decision is NO, so that in fact the second timer T2 has not yet concluded its timing and has not yet reached its timed value, thus indicating that the time represented by the timed value of the second timer T2 has not yet elapsed since the step ST7 above was performed, then the flow of control returns again to this decision step ST8, thus to execute a tight loop until the decision result becomes YES and the time represented by the timed value of the second timer T2 has indeed elapsed since the step ST7 above was performed.

In the next step ST9, the microcomputer 14 inputs the digitalized cuff pressure data Pc(i) fromm the A/D converter 13, and then the flow of control passes next to the step ST10.

In the next step ST10, the microcomputer 14 detects the pulse wave component Pu(i) fronm the cuff pressure data Pc(i), and then the flow of control passes next to the decision step ST11. FIG. 2(a) shows the pulse wave component value, with time taken along the horizontal axis.

Now, it is common to use an analog means including a band pass filter for detecting the pulse wave component, but according to this first preferred embodiment of the electronic blood pressure meter of the present invention a digital filter based upon an arithmetic process performed by the microcomputer 14 is utilized. In this digital filter type arithmetic process, the data Pc(i) obtained by the current sampling is set as a variable x:

$$x(i) = Pc(i) \qquad (1)$$

Then, the value of a variable y(i) is determined from the values of the previously sampled x(i−1) and the previous y(i−1) according to Equation (2) given below:

$$Ay(i) - By(i-1) = x(i) - x(i-1) \qquad (2)$$

And the current value of yet another variable z(i) is determined from the previous value of this variable z(i−1) and the current and the previously sampled values of the variable y(i) and y(i−1) according to Equation (2) given below:

$$Az(i) - Bz(i-1) = y(i) - By(i-1) \qquad (3)$$

The z(i) obtained from the above equation is the pulse wave component value Pu(i) obtained by the current sampling:

$$Pu(i) = z(i) \qquad (4)$$

And the constants A and B are determined, in this first preferred embodiment of the electronic blood pressure meter of the present invention, to be:

$$A = 0.98 \qquad (5)$$

$$B = 0.95 \qquad (6)$$

For the first ones of these iterative arithmetic processes, when i=1, since the initial variables x(0), y(0), and z(0) fo not exist, their values are taken as being zero.

Since this iterative arithmetic processes for calculating the variables x(i), y(i), and z(i) do not require more than the first previous values thereof, i.e. x(i−1), y(i−1), and z(i−1), to be stored, the memory space in the microcomputer 14 can be advantageously conserved.

After the pulse wave compnent value Pu(i) is thus detected in the step ST10, the flow of control passes next to the decision step ST11. In this decision step ST11, a decision is made as to whether or not the timed value of the first timer T1 is up. If the result of this decision is YES, so that in fact the first timer T1 has concluded its timing and has reached its timed value, thus indicating that the time represented by the timed value of the first timer T1 has elapsed since the step ST6 above was performed, then the flow of control passes next to the step ST12; but, if the result of this decision is NO, so that in fact the first timer T1 has not yet concluded its timing and has not yet reached its timed value, thus indicating that the time represented by the timed value of the first timer T1 has not yet elapsed since the step ST6 above was performed, then the flow of control returns again to the step ST7, thus to execute a loop and to repeat the detection of the pulse wave component Pu(i) until the decision result of this decision step ST11 becomes YES and the time represented by the timed value of the first timer T1 has indeed elapsed since the step ST6 above was performed.

In the next step ST12, the microcomputer 14 computes the pulse wave amplitude Ap(n) from the series of data on the pulse wave component value Pu(i) which were detected during the current counting period of the first timer T1, and then the flow of control passes next to the decision step ST13. The computation of Ap(n) is performed by finding the difference between the maximum value Pumax and the minimum value Pumin extracted from the series of data on the pulse wave component value Pu(i):

$$Ap(n) = Pumax - Pumin \qquad (7)$$

In the next decision step ST13, a decision is made as to whether or not the pulse wave amplitude Ap(n) is increasing. If the result of this decision is YES, so that the pulse wave amplitude Ap(n) is in fact increasing, then the flow of control passes next to the step St14, in which the value of a flag F is set to unity, and next the flow of control passes back to the step ST6, as described above, and the next pulse wave amplitude value Ap(n+1) is computed; but, if the result of this decision is NO, so that the pulse wave amplitude Ap(n) is not in fact increasing, then the flow of control passes next to the decision step ST15.

In this next decisio step ST15, at which point it is definitely determined that the pulse wave amplitude Ap(n) is not in fact currently increasing, the microcomputer 14 makes a decision as to whether or not the current value of the flag F is unity. If the result of this decision is YES, so that the value of the flag F is currently in fact unity, then the flow of control passes next to the step ST16; but, if the result of this decision is NO, so that the value of the flag F is not currently in fact unity, then the flow of control passes next to the step ST21.

In the step ST16, te value of the flag F is set to zero by the microcomputer 14, and then the flow of control passes next to the step ST17.

In this next step ST17, the microcomputer 14 extracts the maximum value Apmax from the data on the pulse wave component Ap(n), and then the flow of control passes next to the step ST18.

In this next step ST18, the background pulse wave amplitude value Ab is computed by the microcomputer 14 from the maximum pulse wave amplitude value Apmax, according to the following equation. which was derived by the present inventors from actual clinical data, and then the flow of control passes next to the step ST19:

$$Ab = 0.12\ Apmax + 0.3 \qquad (8)$$

In the next step ST19, the microcomputer 14 subtracts Ab from each value of the pulse wave amplitude value Ap(n), so as to generate a series of data on the compensated pulse wave amplitude value A'p(n), and at the same time Ab is also subtracted from the maximum pulse wave amplitude value Apmax, so as to generate data on the compensated maximum pulse wave amplitude value A'pmax; and then the flow of control passes next to the step ST20.

In this next step ST20, the microcomputer 14 retrives from its memory the compensated pulse wave amplitude value A'p(n) which is closest to, in the case of the fist preferred embodiment of the electronic blood pressure meter of the present invention, 50% of the above calculated compensated maximum pulse wave amplitude value A'pmax, and the cuff pressure Pc(i) corresponding thereto is set as being the value for the systolic blood pressure SYS of the patient; and then the flow of control passes next back again to the step ST6, as described above, to loop around in a large loop, now for the purpose of determining the diastolic blood pressure DIA of the patient.

In this diastolic blood pressure determination stage of the operation, the processes of the steps ST6 through ST12 are performed, as described above, and the pulse wave amplitude values Ap(n) are computed. In the decision step ST13, now, since already the pulse wave amplitude Ap(n) has reached its maximum value and is now declining as shown in FIG. 2(b), the result of the decision is definitely NO, i.e. it is determined that the pulse wave amplitude is not increasing, and the flow of control definitely advances to the decision step ST15. In this decision step ST15, since previously the value of the flag F was set to zero in the step ST16, the result of the decision definitely is NO, and definitely the flow of control now passes to the step ST21.

In this next step ST21, the microcomputer 14 subtracts the background pulse wave amplitude value Ab from the pule wave amplitude value Ap(n), so as to generate the compensated pulse wave amplitude value A'p(n), and then the flow of control passes next to the decision step ST22.

In this decision step St22, a decision is made as to whether or not the compensated pulse wave amplitude value A'p(n) is less than, in the case of this first preferred embodiment of the electronic blood pressure meter of the present invention, 70% of the above calculated compensated maximum pulse wave amplitude value A'pmax. If the result of this decision is YES, so that the compensated pulse wave amplitude value A'p(n) has (just) now become less than 70% of the compensated maximum pulse wave amplitude value A'pmax, then the flow of control passes next to the step ST23; but, if the result of this decision is NO, so that the compensated pulse wave amplitude value A'p(n) has not yet become less than 70% of the compensated maximum pulse wave amplitude value A'pmax, then the flow of control passes back to the step ST6, as described above, and the next pulse wave amplitude value Ap(n+1) is computed.

In this next step ST23, at which program point it has been determined that the compensated pulse wave amplitude value A'p(n) has become less than 70% of the compensated maximum pulse wave amplitude value A'pmax, the microcomputer 14 retrieves the compensated pulse wave amplitude value A'p(n) which is closest to 70% of said compensated maximum pulse wave amplitude value A'pmax (but preceded by the appearance of said compensated maximum pulse wave amplitude value A'pmax), and the cuff pressure Pc(i) corresponding thereto is set as being the value for the diastolic blood pressure DIA of the patient; and then the flow of control passes next to the step ST24.

Finally, in this next step ST24, the microcomputer 14 displays the results of its determinations, i.e. the determined systolic blood pressure SYS and the determined diastolic blood pressure DIA of the patient, upon the display unit 5, and then the flow of control passes next to the step ST25. In this next and final program step ST25, the microcomputer 14 so controls the vent valve 10 as to rapidly vent the air in the cuff 2, so as to allow said cuff 2 to be promptly removed from the arm of the patient, and then the flow of control passes next to exit this program, without doing anything further.

In the above described first preferred embodiment of the electronic blood pressure meter of the present invention, the background pulse wave amplitude Ab was computed from the maximum pulse wave amplitude value Apmax, but this is not to be taken as being limitative of the present invention; in an alternative embodiment, it would be possible to compute said background pulse wave amplitude Ab from other values, such as from the rate of increase of the pulse wave amplitude. Alternatively, in practice, said background pulse wave amplitude Ab could be set to be a constant, since actually it is found to vary relative little between one individual and another.

Further, in the above described first preferred embodiment of the electronic blood pressure meter of the present invention, the background pulse wave amplitude Ab was used as the compensating parameter for the pulse wave amplitude, but, again, this is not to be taken as being limitative of the present invention; in an alternative embodiment, it would be possible to use some other values as said compensating parameter.

Thus, according to this first preferred embodiment of the electronic blood pressure meter of the present invention, the reproducibility of measurement is enhanced, by the compensation parameter for the pulse wave amplitude value reflecting the influence of the background pulse wave upon the measurement results, and compensating for such influence. In this case, even when the patient is obese, even highly obese, the pulse wave amplitude value corresponding to a certain determinate fraction of the maximum amplitude of said pulse wave can always be reliably and definitely extracted, and the systolic and diastolic blood pressures of the patient can be reliably measured without any risk of failure.

The Second Preferred Embodiment

Figure 6A:
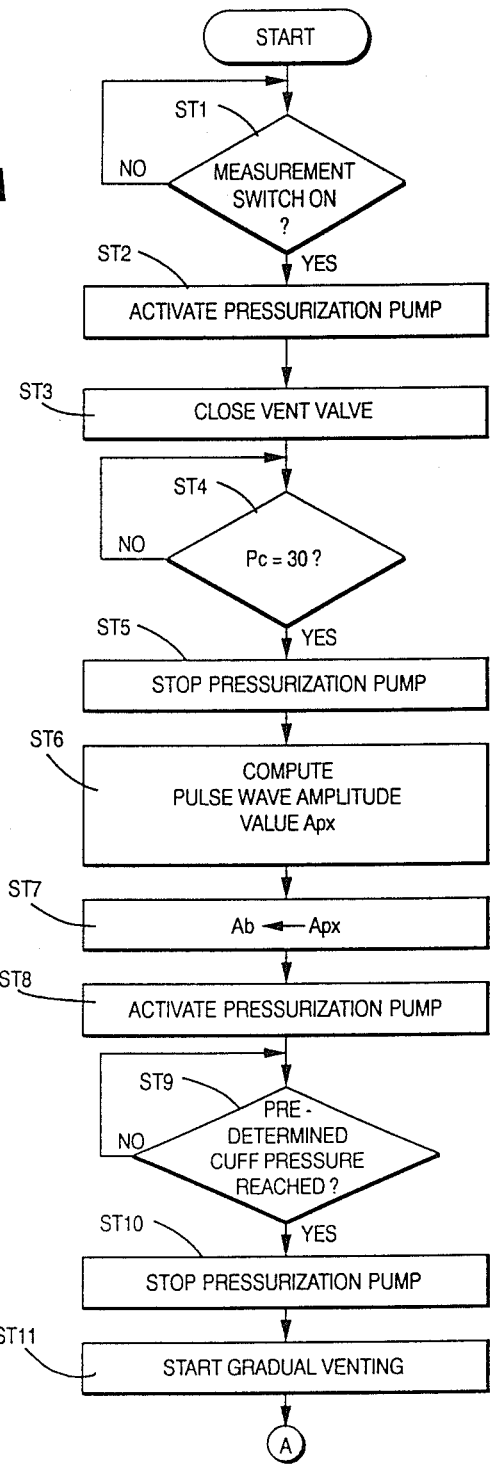
FIG. 6a and FIG. 6b are a flow chart, similar to FIG. 5 for the first preferred embodiment, for illustrating the operation of a portion of a program stored in and obeyed by a micro computer incorporated in said circuit of FIG. 4, in order to realize the operation of the second preferred embodiment of the electronic blood pressure meter of the present invention.
Figure 6B:
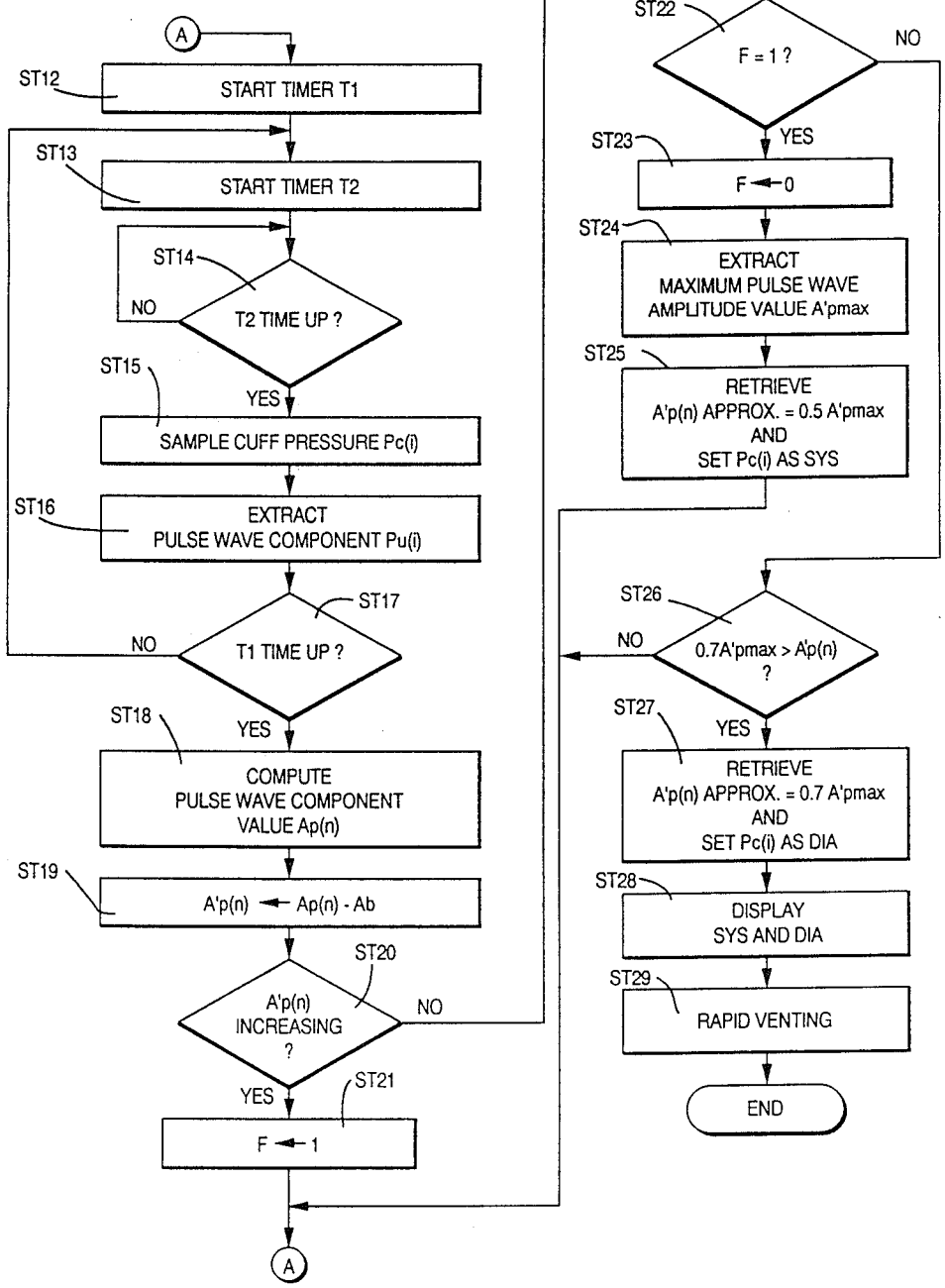

The second preferred embodiment of the electronic blood pressure meter of the present invention will now be described with regard to its function, with reference to FIG. 6.

Construction

The physical construction of this second preferred embodiment of the electronic blood pressure meter of the present invention is substantially the same as that of the first preferred embodiment as described above and as shown in FIGS. 3 and 4, and accordingly detailed description thereof will be eschewed in the interests of brevity of explanation.

Basic Operation

First, an explanaion will be given of the basic principle of operation of this second preferred embodiment of the electronic blood pressure meter of the present invention. As indicated in FIG. 2(b) and discussed previously, the background pulse wave amplitude value is designated as "Ab". As mentioned before, this background pulse wave amplitude value is substantially constant irrespective of the magnitude of the cuff pressure. Therefore, when the cuff pressure is set to a certain cuff pressure value outside or beyond the range of blood pressure determination, i.e. to a cuff pressure value with which no true pulse wave can be detected because the cuff pressure either is substantially higher than the systolic blood pressure of the patient or is substantially lower than the diastolic blood pressure of the patient, in other words to a cuff pressure outside of the range of cuff pressure denoted in the prior art illustration of FIG. 1(a) as the range Z, the pulse wave that can be detected is nothing but the background pulse wave amplitude value. Therefore, by detecting this amplitude value Ab of the background pulse wave at such a time, and by subtracting it from the series of data relating to the pulse wave amplitude value Ap(n) as shown in FIG. 2(b), it is possible to obtain a series of data for the background compensated pulse wave amplitude value A'p(n), as shown in FIG. 2(c), free from the influence of the background pulse wave, thus allowing accurate blood pressure determination to be possible.

When blood pressure values are determined according to this data on the background subtracted or compensated pulse wave amplitude value A'p(n), errors and lack of reproducibility of blood pressure measurement are avoided, and thereby, even when the patient is obese, and therefore the curve of the pulse wave amplitude Ap is relatively flat, the background compensated pulse wave value A'p(n) which corresponds to a certain fraction of the maximum value A'pmax thereof can be easily and reliably determined, and no substantial problems of error or of indefiniteness in determining the time points S and D are caused, such as were present in the prior art described earlier in this specification with reference to FIGS. 1(a) through 1(d) and particularly with reference to FIG. 1(d).

The certain cuff pressure value outside or beyond the range of blood pressure determination, i.e. outside of the range of cuff pressure denoted in the prior art illustration of FIG. 1(a) as the range Z, may conveniently be set to be 30 mmHg.

Operation

This second preferred embodiment of the electronic blood pressure meter of the present invention operates as will now be described, according to a program stored in the microcomputer 14; again, this program will not be paticularly described herein in detail with regard to its programming steps, but only with regard to its functions and with regard to a flow chart thereof, because again the details of the programming for implementing such functions can be easily supplemented by one of ordinary skill in the programming art relevant to the particular microcomputer which it is decided to utilize, based upon the functional disclosures set out in this specification. In this second preferred embodiment, the operation of the controller is determined according to the flow chart shown in FIG. 6a and FIG. 6b. This flow chart will now be explained.

First of all, the cuff 2 is wrapped by an operator around the upper arm of the patient whose blood pressure it is desired to measure, and then the power switch 6 is turned on.

When the power switch 6 is turned on to initiate the operation of the FIG. 6 program, the microcomputer 14 first determines, in the decision step ST1, whether or not the measurement switch 7 is turned on. If in fact the measurement switch 7 is not turned on, then the flow of control returns to this decision step ST1 again, so that the microcomputer 14 loops around and around without advancing, and the system remains in a stand by state until in fact the measurement switch 7 is turned on. On the other hand, when said measurement switch 7 is turned on, the flow of control passes to the next step ST2.

In the step ST2, reached when the measurement switch 7 is turned on as explained above, the microcomputer 14 activates the pressurization pump 9, so as to start pressurizing the cuff 2; and then the flow of control passes next to the next step ST3. In this next step ST3, the microcomputer 14 closes the vent valve 10, and then the flow of control passes next to the decision step ST4. At this point, the pressure sensor 13 is producing an electrical signal representative of the pressure Pc in the cuff 2, and the cuff 2 is being gradually inflated.

Then, in the decision step ST4, a decision is made as to whether or not the cuff pressure Pc, as indicated by the output electrical signal of the pressure sensor 13, has reached a determinate threshold value, which as mentioned above may be equal to 30 mmHg. If the result of this decision is YES, so that the cuff pressure Pc has in fact reached this determinate threshold value of exemplarily 30 mmHg, then the flow of control passes next to the step ST5; but, if the result of this decision is NO, so that the cuff pressure Pc has not yet in fact reached this determinate threshold value, then the flow of control passes next to this decision step ST3 again, so as to loop around until the cuff pressure Pc does reach the determinate threshold value of exemplarily 30 mmHg.

In the next step ST5, the microcomputer 14 stops the operation of the pressurization pump 9, and then the flow of control passes next to the step ST6. In this next step ST6, the microcomputer 14 determines the current value of the pulse wave amplitude Apx, in the same manner as the pulse wave amplitude value Ap(n) is calculated as will be explained later with regard to the steps ST12 through ST18; and then the flow of control passes next to the step ST7. And then, in this next step ST7, the microcomputer 14 sets this pulse wave amplitude value APx as the background pulse wave amplitude value Ab; and then the flow of control passes next to the step ST8. In this next step ST8, the microcomputer 14 again starts the operation of the pressurization pump 9, and then the flow of control passes next to the decision step ST9.

Then, in this decision step ST9, a decision is made as to whether or not the cuff pressure Pc, as indicated by the output electrical signal of the pressure sensor 13, has reached another determinate threshold value for blood pressure measurement. If the result of this decision is YES, so that the cuff pressure Pc has in fact reached this determinate threshold value, then the flow of control passes next to the step ST10; but, if the result of this decision is NO, so that the cuff pressure Pc has not yet in fact reached this determinate threshold value, then the flow of control passes next to this decision step ST9 again, so as to loop around until the cuff pressure Pc does reach this new determinate threshold value.

In the next step ST10, the microcomputer 14 stops the operation of the pressurization pump 9, and then the flow of control passes next to the step ST11. And, in this next step ST11, the microcomputer 14 actuates the vent valve 10 so as to start gradually venting the cuff 2, i.e. so as to start gradually lowering the cuff pressure, and then the flow of control passes next to the step ST12.

In this next step ST12, which also is the step back to which the flow of control returns in a large loop after the step ST21 and also after the step ST25 and after the NO branch from the decision step 26 to be described later, the microcomputer 14 starts the counting process of a first timer, designated as T1. Again, this timer T1 is for determining the frequency of computing the pulse wave amplitude value Ap(n) from the pulse wave component, and its timed value is normally set to be between about 1 second and about 2 seconds. And then the flow of control passes next to the step ST13.

In this next step ST13, which also is the step back to which the flow of control returns in a smaller loop after a NO decision in the decision step ST17 to be described later, the microcomputer 14 starts the counting process of a second timer, designated as T2. This timer T2 is, again, for determining the sampling frequency of the microcomputer 14 when it takes in a value representative of the cuff pressure from the A/D converter 13, and its timed value is normally set to be between about 10 ms and about 50 ms. And then the flow of control passes next to the decision step ST14.

In this decision step ST14, a decision is made as to whether or not the timed value of the second timer T2 is up. If the result of this decision is YES, so that in fact the second timer T2 has concluded its timing and has reached its timed value, thus indicating that the time represented by the timed value of the second timer T2 has elapsed since the step ST13 above was performed, then the flow of control passes next to the step ST15;

but, if the result of this decision is NO, so that in fact the second timer T2 has not yet concluded its timing and has not yet reached its timed value, thus indicating that the time represented by the timed value of the second timer T2 has not yet elapsed since the step ST13 above was performed, then the flow of control returns again to this decision step ST14, thus to execute a tight loop until the decision result becomes YES and the time represented by the timed value of the second timer T2 has indeed elapsed since the step ST13 above was performed.

In the next step ST15, the microcomputer 14 inputs the digitalized cuff pressure data Pc(i) from the A/D converter 13, and then the flow of control passes next to the step ST16.

In the next step ST16, the microcomputer 14 detects the pulse wave component Pc(i) from the cuff pressure data Pc(i). According to this second preferred embodiment of the electronic blood pressure meter of the present invention, a digital filter based upon an arithmetic process performd by the microcomputer 14 is utilized, the same as in the case of the first preferred embodiment; accordingly, detailed description thereof will be eschewed in the interests of brevity of disclosure. After the pulse wave component value Pu(i) is thus detected in this step ST16, the flow of control passes next to the decision step ST17.

In this decision step ST17, a decision is made as to whether or not the timed value of the first timer T1 is up. If the result of this decision is YES, so that in fact the first timer T1 has concluded its timing and has reached its timed value, thus indicating that the time represented by the timed value of the first timer T1 has elapsed since the step ST12 above was performed, then the flow of control passes next to the step ST18; but, if the result of this decision is NO, so that in fact the first timer T1 has not yet concluded its timing and has not yet reached its timer value, thus indicating that the time represented by the timed value of the first timer T1 has not yet elapsed since the step ST12 above was performed, then the flow of control returns again to the step ST13, thus to execute a loop and to repeat the detection of the pulse wave component Pu(i) until the decision result of this decision step ST17 becomes YES and the time represented by the timed value of the first timer T1 has indeed elapsed since the step ST12 above was performed.

In the next step ST18, the microcomputer 14 computes the pulse wave amplitude Ap(n) from the series of data on the pulse wave component value Pu(i) which were detected during the current counting period of the first timer T1, and then the flow of control passes next to the step ST19. The computation of Ap(n) is, as before, performed by finding the difference between the maximum value Pumax and the minimum value Pumin extracted from the series of data on the pulse wave component value Pu(i), i.e, as Ap(n)=Pumax−Pumin. Then, in the next step ST19, the microcomputer 14 subtracts the previously determined background pulse wave amplitude value Ab from the background pulse wave amplitude value Ab from the pulse wave amplitude value Ap(n), so as to generate the compensated pulse wave amplitude value A'p(n), and then the flow of control passes next to the decision step ST20.

In this next decision step ST20, a decision is made as to whether or not the compensated pulse wave amplitude A'p(n) is increasing. If the result of this decision is YES, so that the compensated pulse wave amplitude A'p(n) is in fact increasing, then the flow of control passes next to the step ST21, in which the value of a flag F is set to unity, and next the flow of control passes back to the step ST12, as described above, and the next pulse wave amplitude value Ap(n+1) is computed; but, if the result of this decision is NO, so that the compensated pulse wave amplitude A'p(n) is not in fact increasing, then the flow of control passes next to the decision step ST22.

In this next decision step ST22, at which point it is definitely determined that the pulse wave amplitude A'p(n) is not in fact currently increasing, the microcomputer 14 makes a decision as to whether or not the current value of the flag F is unity. If the result of this decision is YES, so that the value of the flag F is currently in fact unity, then the flow of control passes next to the step ST23; but, if the result of this decision is NO, so that the value of the flag F is not currently in fact unity, then the flow of control passes next to the step ST26.

In the step ST23, the value of the flag F is set to zero by the microcomputer 14, and then the flow of control passes next to the step ST24.

In this next step ST24, the microcomputer 14 extracts the maximum value A'pmax from the data on the compensated pulse wave component A'p(n), and then the flow of control passes next to the step ST25.

In this next step ST25, the microcomputer 14 retrieves from its memory the compensated pulse wave amplitude value A'p(n) which is closest to, in the case of this second preferred embodiment of the electronic blood pressure meter of the present invention, 50% of the maximum compensated pulse wave amplitude value A'pmax, and the cuff pressure Pc(i) corresponding thereto is set as being the value for the systolic blood pressure SYS of the patient; and then the flow of control passes next back again to the step ST12, as described above, to loop around in a large loop, now for the purpose of determining the diastolic blood pressure DIA of the patient.

In this diastolic blood pressure determination stage of the operation, the processes of the steps ST12 through ST19 are performed, as described above, and the compensated pulse wave amplitude values A'p(n) are computed. In the decision step ST20, now, since already the compensated pulse wave amplitude A'p(n) has reached its maximum value and is now declining as shown in FIG. 2(b), the result of the decision is definitey NO, i.e. it is determined that the pulse wave amplitude is not increasing, and the flow of control definitely advances to the decision step ST22. In this decision step ST22, since previously the value of the flag F was set to zero in the step ST23, the result of the decision definitely is NO, and definitely the flow of control now passes to the decision step ST26.

In this next decision step ST26, a decision is made as to whether or not the compensated pulse wave amplitude value A'p(n) is less than, in the case of this second preferred embodiment of the electronic blood pressure meter of the present invention, 70% of the above calculated compensated maximum pulse wave amplitude value A'pmax. If the result of this decision is YES, so that the compensated pulse wave amplitude value A'p(n) has (just) now become less than 70% of the compensated maximum pulse wave amplitude value A'pmax, then the flow of control passes next to the step ST27; but, if the result of this decision is NO, so that the compensated pulse wave amplitude value A'p(n) has not yet become less than 70% of the compensated maximum pulse wave amplitude value A'pmax, then the flow of control passes back to the step ST12, as described above, and the next compensated pulse wave amplitude value A'p(n+1) is computed.

In this next step ST27, at which program point it has been determined that the compensated pulse wave amplitude value A'p(n) has become less than 70% of the compensated maximum pulse wave amplitude value A'pmax, the microcomputer 14, as in the case of the first preferred embodiment, retrieves the compensated pulse wave amplitude value A'p(n) which is closest to 70% of said compensated maximum pulse wave amplitude value A'pmax (but preceded by the appearance of said compensated maximum pulse wave amplitude value A'pmax), and the cuff pressure Pc(i) corresponding thereto is set as being the value for the diastolic blood pressure DIA of the patient; and then the flow of control passes next to the step ST28, in which, as before, the microcomputer 14 displays the results of its determinations, i.e. the determined systolic blood pressure SYS and the determined diastolic blood pressure DIA of the patient, upon the display unit 5. Then the flow of control passes next to the step ST29, and in this next and final program step ST29 the microcomputer 14 so controls the vent valve 10 as to rapidly vent the air in the cuff 2, so as to allow said cuff 2 to be promptly removed from the arm of the patient, and then the flow of control passes next to exit this program, without doing anything further.

In the above described second preferred embodiment of the electronic blood pressure meter of the present invention, the background pulse wave amplitude Ab was determined in a stage of initial cuff inflation where the cuff pressure was relatively low, i.e. was outside the range shown by Z in FIG. 1(a) on its lower side and was substantially lower than the diastolic blood pressure DIA of the patient; but this is not to be taken as being limitative of the present invention, and, in an alternate embodiment, it would be possible to determine said background pulse wave amplitude AB in a stage of late cuff inflatin where the cuff pressure was relatively high, i.e. was outside the range shown by Z in FIG. 1(a) on its higher side and was substantially higher than the systolic blood pressure SYS of the patient. This would be done by first over pressurizing the cuff 2, and then determining the background pulse wave amplitude Ab before, or while initially venting, said cuff 2.

The Third Preferred Embodiment

Figure 8A:
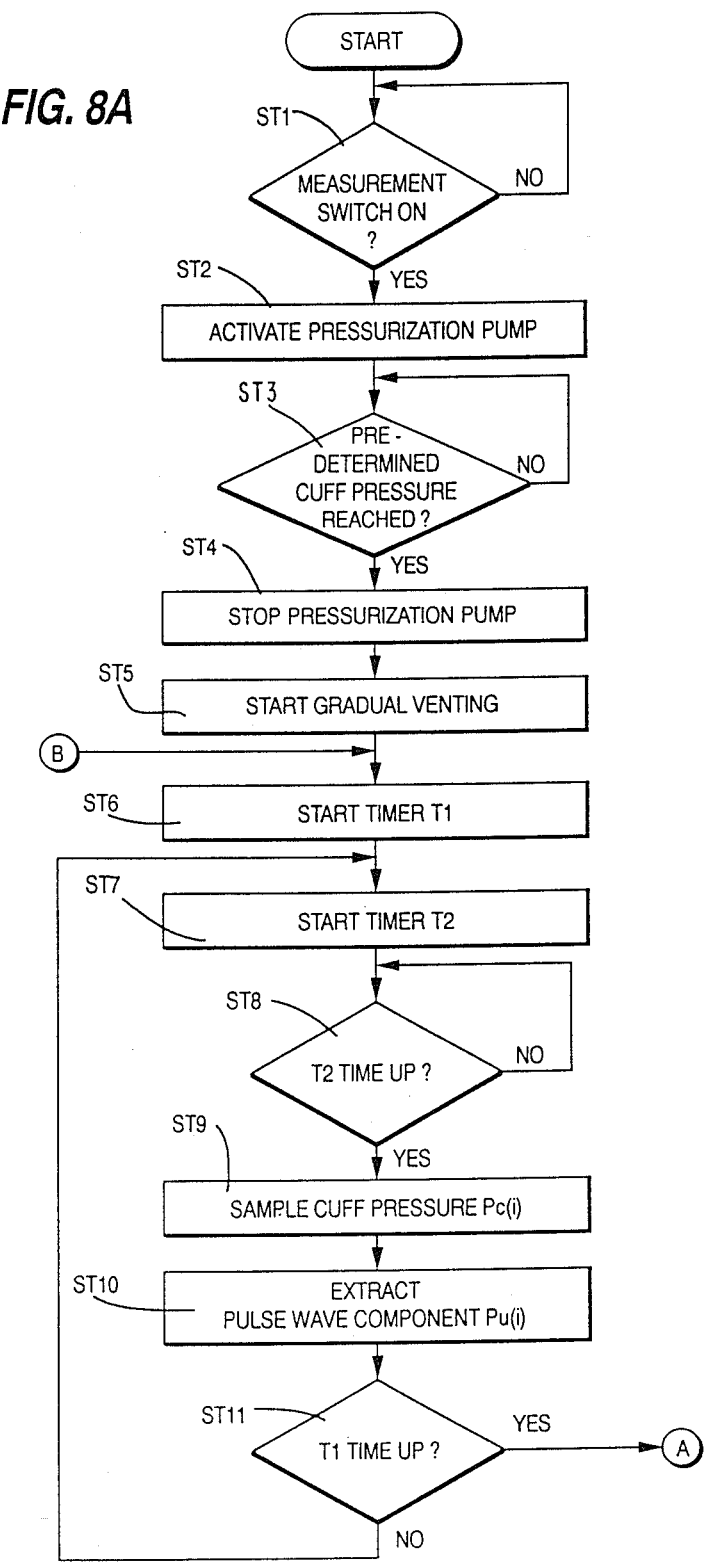
FIG. 8a and FIG. 8b are a flow chart, similar to FIG. 5 for the first preferred embodiment and to FIG. 6 for the second preferred embodiment, for illustrating the operation of a portion of a program stored in and obeyed by a micro computer incorporated in said circuit of FIG. 4, in order to realize the operation of the third preferred embodiment of the electronic blood pressure of the present invention.
Figure 8B:
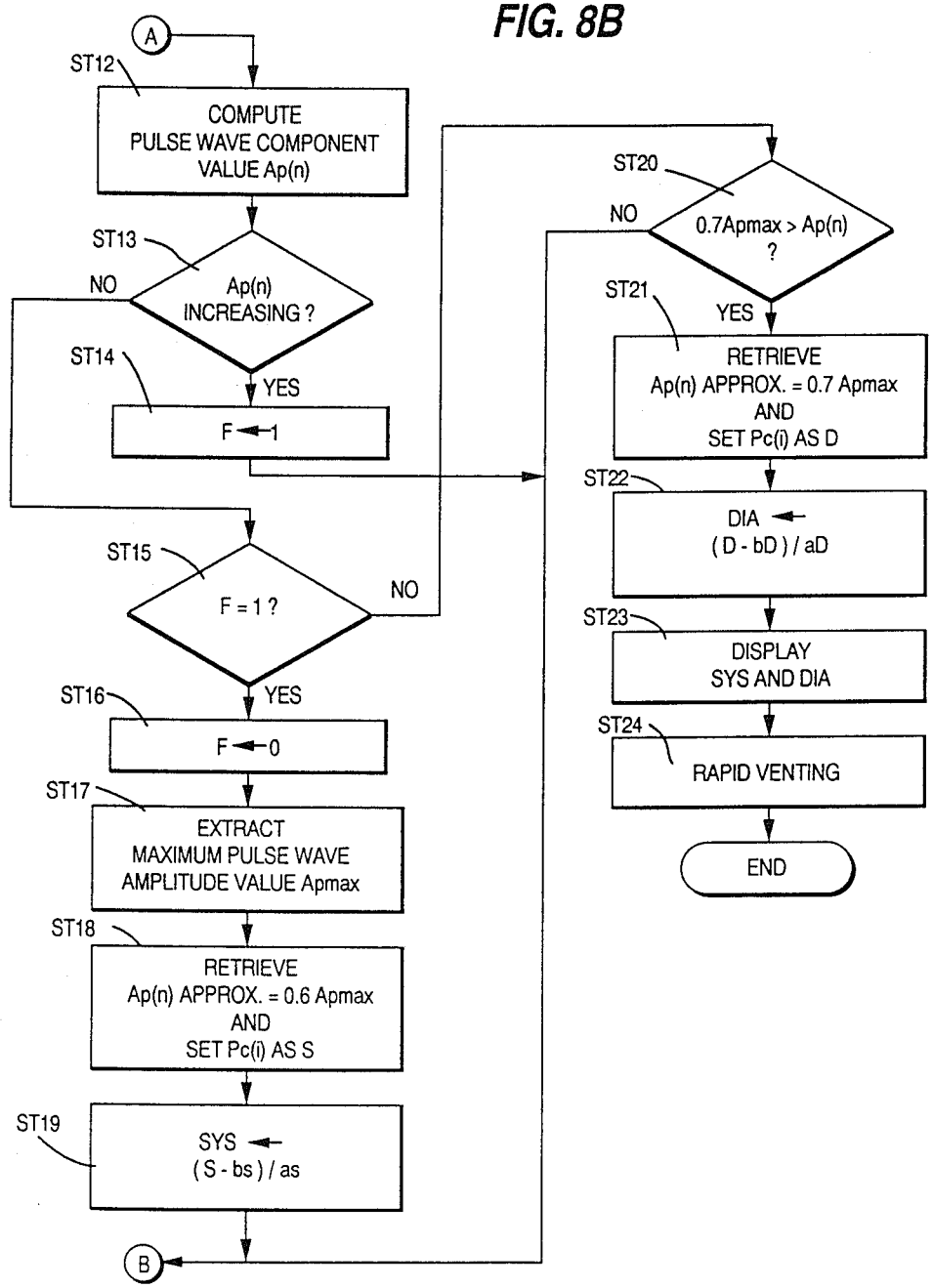

The third preferred embodiment of the electronic blood pressure meter of the present invention will now be described with regard to its function, with reference to FIG. 8.

Construction

The physical construction of this third preferred embodiment of the electronic blood pressure meter of the present invention is substantially the same as that of the first and the second preferred embodiments as described above and as shown in FIGS. 3 and 4, and accordingly detailed description thereof will be eschewed in the interests of brevity of explanation.

Basic Operation

First, an explanation will be given of the basic principle of operation of this third preferred embodiment of the electronic blood pressure meter of the present invention, and the meaning of the threshold values for determining blood pressures and the compensating equation for arithmetic compensation operation will be explained.

The threshold value for the pulse wave amplitude for determining the systolic blood pressure of the patient, in the case of this third preferred embodiment of the electronic blood pressure meter of the present invention, is set as being 60% of the maximum pulse wave amplitude value Apmax on the high cuff pressure side thereof where said pulse wave amplitude is increasing along with time as the cuff pressure is steadily decreased, and the threshold value for said pulse wave amplitude for determining the diastolic blood pressure of the patient is set as being 70% of the maximum pulse wave amplitude value Apmax on the low cuff pressure side thereof where said pulse wave amplitude is decreasing along with time as the cuff pressure is steadily decreased.

And, as the compensation equation for the arithmetic compensation operation, the following equation (9) is used for the systolic blood pressure:

$$SYS = (S - bs)/as \tag{9}$$

$$\text{where } as = 0.91 \tag{10}$$

$$\text{and } bs = 11.2 \text{ mmHg} \tag{11}$$

Here, SYS is the finally determined value for the systolic blood pressure of the patient, while S is the systolic blood pressure value (referred to as the systolic pressure value candidate hereinafter) as determined by the blood pressure determining means before this arithmetic compensating operation is performed. Equation (5) is obtained by solving equation (a) described earlier in this specification in terms of the systolic blood pressure value Saus.

Similarly, as the compensation equation for the arithmetic compensation operation, the following equation (12) is used for the diastolic blood pressure:

$$DIA = (D - bd)/ad \tag{12}$$

$$\text{where } ad = 0.91 \tag{13}$$

$$\text{and } bd = 7.5 \text{ mmHg} \tag{14}$$

Here, DIA is the finally determined value for the diastolic blood pressure of the patient, while D is the diastolic blood pressure value (referred to as the diastolic pressure value candidate hereinafter) as determined by the blood pressure determining means before this arithmetic compensating operation is performed. Equation (5) is obtained by solving equation (b) described earlier in this specification in terms of the diastolic blood pressure value Daus.

Operation

This third preferred embodiment of the electronic blood pressure meter of the present invention operates as will now be described, again according to a program stored in the microcomputer 14; as before, this program will not be particularly described herein in detail with regard to its programming steps, but only with regard to its functions and with regard to a flow chart therof, because again the details of the programming for implementing such functions can be easily supplemented by one of ordinary skill in the programming art relevant to the particular microcomputer which it is decided to utilize, based upon the functional disclosures set out in this specification. In this third preferred embodiment, the operation of the controller is determined according to the flow chart shown in FIG. 8a and FIG. 8b. This flow chart will now be explained.

First of all, the cuff 2 is wrapped by an operator around the upper arm of the patient whose blood pressure it is desired to measure, and then the power switch 6 is turned on.

When the power switch 6 is turned on to initiate the operation of the FIG. 8 program, the microcomputer 14 first determines, in the decision step ST1, whether or not the measurement switch 7 is turned on. If in fact the measurement switch 7 is not turned on, then the flow of control returns to this decision step ST1 again, so that the microcomputer 14 loops around and around without advancing, and the system remains in a stand by state until in fact the measurement switch 7 is turned on. On the other hand, when said measurement switch 7 is turned on, then the flow of control passes to the next step ST2.

In the step ST2, reached when the measurement switch 7 is turned on as explained above, the microcomputer 14 activates the pressurization pump 9, so as to start pressurizing the cuff 2; and then the flow of control passes next to the next decision step ST3. At this point, the pressure sensor 13 is producing an electrical signal representative of the pressure Pc in the cuff 2.

Then, in this decision step ST3, a decision is made as to whether or not the cuff prressure Pc, as indicated by the output electrical signal of the pressure sensor 13, has reached a determinate threshold value. If the result of this decision is YES, so that the cuff pressure Pc has in fact reached this determinate threshold value, then the flow of control passes next to the step ST4; but, if the result of this decision is NO, so that the cuff pressure Pc has not yet in fact reached this determinate threshold value, then the flow of control passes next to this decision step ST3 again, so as to loop around in a tight loop until the cuff prressure Pc does reach the determinate threshold value.

In the next step ST4, the microcomputer 14 stops the operation of the pressurization pump 9, and then the flow of control passes next to the step ST5. And, in this next step ST5, the microcomputer 14 actuates the vent valve 10 so as to start gradually venting the cuff 2, i.e. so as to start gradually lowering the cuff pressure, and then the flow of control passes next to the step ST6.

In this next step ST6, which also is the step back to which the flow of control returns in a large loop after the step ST19, after the step ST14, and also in the NO branch from the decision step ST20 to be described later, the microcomputer 14 starts the counting process of a first timer, designated as T1. This timer T1 is for determining the frequency of computing the pulse wave amplitude value Ap(n) from the pulse wave component, and its timed value is normally set to be between about 1 second and about 2 seconds. And then the flow of control passes next to the step ST7.

In this next step ST7, which also is the step back to which the flow of control returns in a smaller loop after a NO decision in the decision step ST11 to be described later, the microcomputer 14 starts the counting process of a second timer, designated as T2. This timer T2 is for determining the sampling frequency of the microcomputer 14 when it takes in a value representative of the cuff pressure from the A/D converter 13, and its timed value is normally set to be between about 10 ms and about 50 ms. And then the flow of control passes next to the decision step ST8.

In this decision step ST8, a decision is made as to whether or not the timed value of the second timer T2 is up. If the result of this decision is YES, so that in fact the second timer T2 has concluded its timing and has reached its timed value, thus indicating that the time represented by the timed value of the second timer T2 has elapsed since the step ST7 above was performed, then the flow of control passes next to the step ST9; but, if the result of this decision is NO, so that in fact the second timer T2 has not yet concluded its timing and has not yet reached its timed value, thus indicating that the time represented by the timed value of the second timer T2 has not yet elapsed since the step ST7 above was performed, then the flow of control returns again to this decision step ST8, thus to execute a tight loop until the decision result becomes YES and the time represented by the timed value of the second timer T2 has indeed elapsed since the step ST7 above was performed.

In the next step ST9, the microcomputer 14 inputs the digitalized cuff pressure data Pc(i) from the A/D converter 13, and then the flow of control passes next to the step ST10.

In the next step ST10, the microcomputer 14 detects the pulse wave component Pu(i) from the cuff pressure data Pc(i), and then the flow of control passes next to the decision step ST11. As before, although it is common to use an anaog means including a band pass filter for detecting the pulse wave component, nevertheless according to this third preferred embodiment of the electronic blood pressure meter of the present invention a digital filter based upon an arithmetic process performed by the microcomputer 14 is utilized, of the same type as in the first and second preferred embodiments. After the pulse wave component value Pu(i) is thus detected in the step ST10, the flow of control passes next to the decision step ST11.

In this decision step ST11, a decision is made as to whether or not the timed value of the first timer T1 is up. If the result of this decision is YES, so that in fact the first timer T1 has concluded its timing and has reached its timed value, thus indicating that the time represented by the timed value of the first timer T1 has elapsed since the step ST6 above was performed, then the flow of control passes next to the step ST12; but, if the result of this decisionis NO, so that in fact the first timer T1 has not yet concluded its timing and has not yet reached its timed value, thus indicating that the time represented by the timed value of the first timer T1 has not yet elapsed since the step ST6 above was performed, then the flow of control returns back again to the step ST7, thus to execute a loop and to repeat the detection of the pulse wave component Pu(i) until the decision result of this decision step ST11 becomes YES and the time represented by the timed value of the first timer T1 has indeed elapsed since the step ST6 above was performed.

In the next step ST12, the microcomputer 14 computes the pulse wave amplitude Ap(n) from the series of data on the pulse wave component value Pu(i) which were detected during the current counting period of the first timer T1, and then the flow of control passes next to the decision step ST13. The computation of Ap(n) is performed, as before, by finding the difference between the maximum value Pumax and the minimum value Pumin extracted from the series of data on the pulse wave component value Pu(i), i.e. as Ap(n)=Pumax—Pumin.

In the next decision step ST13, a decision is made as to whether or not the pulse wave amplitude Ap(n) is increasing. If the result of this decision is YES, so that the pulse wave amplitude Ap(n) is in fact increasing, then the flow of control passes next to the step ST14, in which the value of a flag F is set to unit, and next the flow of control passes back to the step ST6, as described above, and the next pulse wave amplitude value Ap(n+1) is computed; but, if the result of this decision is NO, so that the pulse wave amplitude Ap(n) is not in fact increasing, then the flow of control passes next to the decision step ST15.

In this next decision step ST15, at which point it is definitely determined that the pulse wave amplitude Ap(n) is not in fact currently increasing, the microcomputer 14 makes a decision as to whether or not the current value of the flag F is unity. If the result of this decision is YES, so that the value of the flag F is currently in fact unity, then the flow of control passes next to the step ST16; but, if the result of this decision is NO, so that the value of the flag F is not currently in fact unity, then the flow of control passes next to the decision step ST20.

In the step ST16, the value of the flag F is set to zero by the microcomputer 14, and then the flow of control passes next to the step ST17.

In this next step ST17, the microcomputer 14 extracts the maximum value Apmax from the data on the pulse wave component Ap(n), and then the flow of control passes next to the step ST18.

In this next step ST18, the microcomputer 14 retrieves from its memory the pulse wave amplitude value Ap(n) which is closest to, in the case of this third preferred embodiment of the electronic blood pressure meter of the present invention, 60% of the above calculated maximum pulse wave amplitude value Apmax, and the cuff pressure Pc(i) corresponding thereto is set as being the value for the candidate systolic blood pressure S of the patient. Then, the flow of control passes next to the step ST19.

In this next step ST19, the microcomputer 14 performs the arithmetic compensation operation on this candidate systolic blood pressure S, thus to determine the final systolic blood pressure SYS of the patient; and then the flow of control passes next back again to the step ST6, as described above, to loop around in a large loop, now for the purpose of determining the diastolic blood pressure DIA of the patient.

In this diastolic blood pressure determination stage of the operation, the processes of the steps ST6 through ST12 are performed, as described above, and the pulse wave amplitude values Ap(n) are computed. In the decision step ST13, now, since already the pulse wave amplitude Ap(n) has reached its maximum value and is now declining, the reslt of the decision is definitely NO, i.e. it is determined that the pulse wave amplitude is not increasing, and the flow of control definitely advances to the decision step ST15. In this decision step ST15, since previously the value of the flag F was set to zero in the step ST16, the result of the decision definitely is NO, and definitely the flow of control now passes to the decision step ST20.

In this decision step ST20, a decision is made as to whether or not the pulse wave amplitude value Ap(n) is less than, in the case of this third preferred embodiment of the electronic blood pressure meter of the present invention, 70% of the above calculated maximum pulse wave amplitude value Apmax. If the result of this decision is YES, so that the pulse wave amplitude value Ap(n) has (just) now become less than 70% of the maximum pulse wave amplitude value Apmax, then the flow of control passes next to the step ST21; but, if the result of this decision is NO, so that the pulse wave amplitude value Ap(n) has not yet become less than 70% of the maximum pulse wave amplitude value Apmax, then the flow of control passes back to the step ST6, as described above, and the next pulse wave amplitude value Ap(n+1) is computed.

In the next step ST21, at which program point it has been determined that the pulse wave amplitude value Ap(n) has become less than 70% of the maximum pulse wave amplitude value Apmax, the microcomputer 14 retrieves the pulse wave amplitude value Ap(n) which is closest to 70% of said maximum pulse wave amplitude value Apmax (but preceded by the appearance of said maximum pulse wave amplitude value Apmax), and the cuff pressure Pc(i) corresponding thereto is set as being the candidate diastolic blood pressure value D for the patient; and then the flow of control passes next to the step ST22.

In this next step ST22, the microcomputer 14 performs the arithmetic compensation operation on this candidate diastolic blood pressure D, thus to determine the final diastolic blood pressure DIA of the patient; and then the flow of control passes next to the step ST23.

Finally, in this next step ST23, the microcomputer 14 displays the results of its determinations, i.e. the determined systolic blood pressure SYS and the determined diastolic blood pressure DIA of the patient, upon the display unit 5, and then the flow of control passes next to the step ST24. In this next and final program step ST24, the microcomputer 14 so controls the vent valve 10 as to rapidly vent the air in the cuff 2, so as to allow said cuff 2 to be promptly removed from the armm of the patient, and then the flow of control passes next to exit this program, without doing anything further.

Figure 7A:
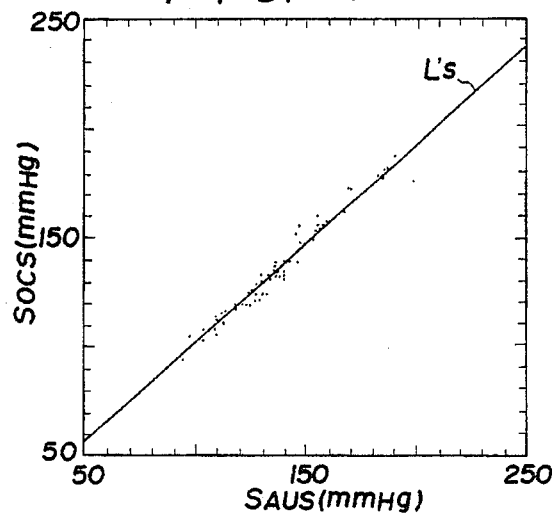
FIG. 7 is a pair of graphs relating to the prior art, FIG. 7(a) showing the correlation between the systolic blood pressure Saus (in mmHg) measured for a patient by using the stethoscopic method and the systolic blood pressure Sosc (in mmHg) measured for the same patient by using a conventional type of electronic blood pressure meter which operates according to the oscillation method, and FIG. 7(b) showing the correlation between the diastolic blood pressure Daus (in mmHg) likewise measured for a patient by using the stethoscopic method and the diastolic blood pressure Dosc (in mmHg) likewise measured for the same patient by using such a conventional type of electronic blood pressure meter which operates according to the oscillation method.
Figure 9A:
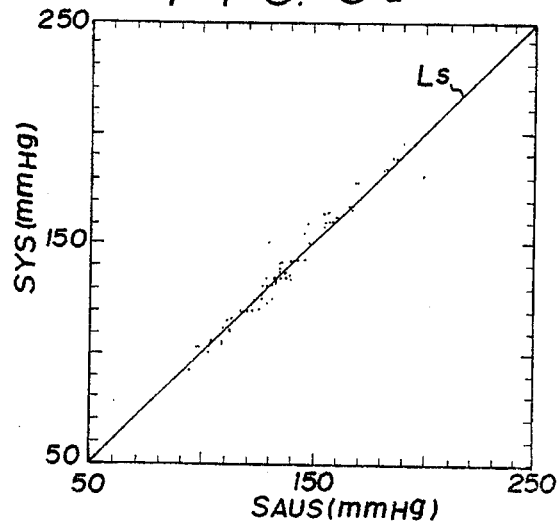
FIG. 9 is a pair of graphs, like the graphs of FIG. 7 but this time relating to the third preferred embodiment of the electronic blood pressure meter of the present invention, FIG. 9(a) showing the correlation between the systolic blood pressure Saus (in mmHg) measured for a patient by using the stethoscopic method and the systolic blood pressure SYS (in mmHg) measured for the same patient by using this third preferred embodiment, and FIG. 9(b) showing the correlation between the diastolic blood pressure Daus (in mmHg) measured for a patient by using the stethoscopic method and the diastolic blood pressure DIA (in mmHg) measured for the same patient by using this third preferred embodiment.

FIG. 9(a) is a graph showing the correlation between the systolic blood pressure Saus (in mmHg) measured for a patient by using the stethoscopic method, and the systolic blood pressure SYS (in mmHg) measured for the same patient by using this third preferred embodiment of the electronic blood pressure meter of the present invention. The points plotted in FIG. 9(a) fall onto the line Ls, which approximately is the line where Saus=SYS. Thus, the systolic blood pressure SYS as measured by this third preferred embodiment of the electronic blood pressure meter of the present invention is free from consistent error, and the problem outlined above with regard to the prior art with reference to FIG. 7(a), that the measured systolic blood pressure tends to be relatively lower for a patient with a relatively high blood pressure and tends to be relatively higher for a patient with a relatively low blood pressure, is prevented.

Figure 7B:
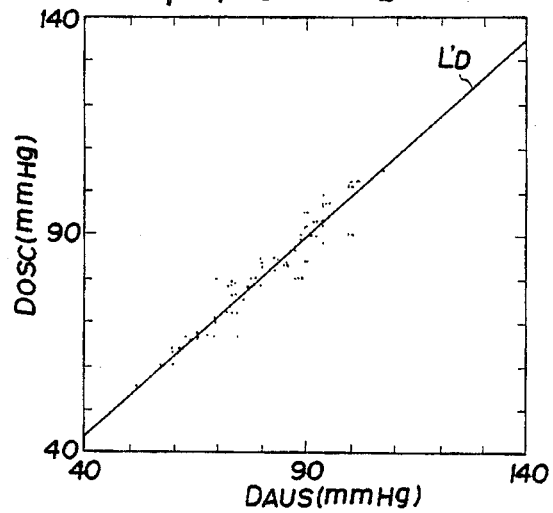
Figure 9B:
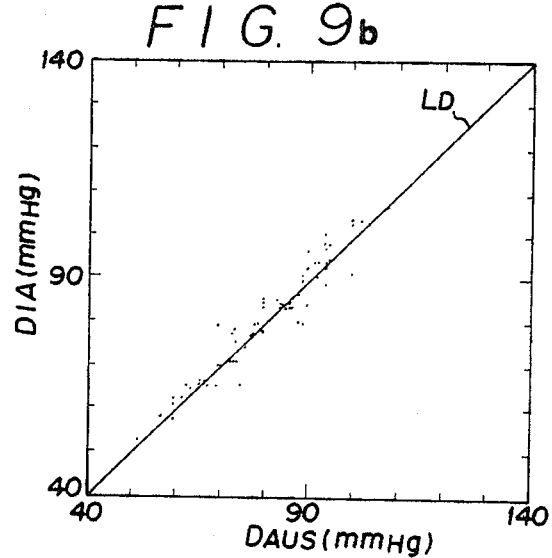

Similarly, FIG. 9(b) is a graph showing the correlation between the diastolic blood pressure Daus (in mmHg) measured for a patient by using the stethoscopic method, and the diastolic blood pressure DIA (in mmHg) measured for the same patient by using this third preferred embodiment of the electronic blood pressure meter of the present invention. The points plotted in FIG. 9(b) fall onto the line Ld, which approximately is the line where Daus=DIA. Thus, the diastolic blood pressure DIA as measured by this third preferred embodiment of the electronic blood pressure meter of the present invention is free from consistent error, and the problem outlined above with regard to the prior art with reference to FIG. 7(b), that the measured diastolic blood pressure tends to be relatively lower for a patient with a relatively high blood pressure and tends to be relatively higher for a patient with a relatively low blood pressure, is likewise prevented.

In the above described third preferred embodiment of the electronic blood pressure meter of the present invention, the threshold value for the pulse wave amplitude determining the candidate systolic blood pressure value S was taken as being 60% of the maximum pulse wave amplitude, but this is not to be taken as being limitative of the present invention; in an alternative embodiment, it would be possible to use a different value. Similarly, in the above described third preferred embodiment of the electronic blood pressure meter of the present invention, the threshold value for the pulse wave amplitude determining the candidate diastolic blood pressure value D was taken as being 70% of the maximum pulse wave amplitude, but this is not to be taken as being limitative of the present invention; in an alternative embodiment, it would again be possible to use a different value. Also, in the above described third preferred embodiment of the electronic blood pressure meter of the present invention, the constants as and bd of the compensation equation (12) were taken, according to equations (13) and (14), as being equal to 0.91 and to 7.5 mmHg respectively, but, again, this is not to be taken as being limitative of the present invention; in an alternative embodiment, it would be possible to utilize other values for these constanfts, possibly in tandem with modification of the threshold values as described proximately above.

Thereby, according to this third preferred embodiment of the electronic blood pressure meter of the present invention, it is possible to obtain reliable measurement both of the systolic blood pressure of the patient and of the diastolic blood pressure of the patient, whether these blood pressures be high or low, without the occurrence of any systematic deviations from the blood pressure values obtained by the stethoscopic method.

Conclusion

Although the present invention has been shown and described in terms of the preferred embodiments thereof, and with reference to the appended drawings, it should not be considered as being particularly limited thereby, since the details of any particular embodiment, or of the drawings, could be varied without, in many cases, departing from the ambit of the present invention. Accordingly, the scope of the present invention is to be considered as being delimited, not by any particular perhaps entirely fortuitous details of the disclosed preferred embodiments, or of the drawings, but solely by the scope of the accompanying claims, which follow.

What is claimed is:

1. An electronic blood pressure meter, comprising:
   (a) a cuff adapted to be fitted around the arm of a patient whose blood pressure is to be measured, said cuff having a cavity;
   (b) means for pressurizing the cavity of said cuff;
   (c) means for gradually depressurizing the cavity of said cuff;
   (d) means for sensing the pressure in the cavity of said cuff, and for producing an output signal representative of the pressure in the cavity;
   (e) means for detecting a pulse wave component in said output signal produced by the sensing means;
   (f) means for determining the amplitude of the pulse wave component detected by said detecting means;
   (g) means for determining values for systolic blood pressure and diastlic blood pressure, according to the amplitude of the pulse wave component and according to the output signal produced by the sensing means; and
   (h) means for performing compensation related to said values for systolic blood pressure and diaastolic blood pressure, comprising:
      (1) means for determining a compensation parameter according to the maximum value of the amplitude of the pulse wave component; and
      (2) means for compensating the amplitude of the pulse wave component by subtracting the compensation parameter therefrom.

2. An electronic blood pressure meter, comprising:
   (a) a cuff adapted to be fitted around the arm of a patient whose blood pressure is to be measured, said cuff having a cavity;
   (b) means for pressurizing the cavity of said cuff;
   (c) means for gradually depressurizing the cavity of said cuff;
   (d) means for sensing the pressure in the cavity of said cuff, and for producing an output signal representative of the pressure in the cavity;
   (e) means for detecting a pulse wave component in said output signal produced by the sensing means;
   (f) means for determining the amplitude of the pulse wave component detected by said detecting means;
   (g) means for determining values for systolic blood pressure and diastolic blood pressure, according to the amplitude of the pulse wave component and according to the output signal produced by the sensing means; and
   (h) means for performing compensation related to said values for systolic blood pressure and diastolic blood pressure, comprising:
      (1) means for determining a compensation parameter according to the value of the amplitude of the pulse wave component in a circumstance in which the pressure in the cuff is outside a range of blood pressure measurement; and
      (2) means for compensating the amplitude of the pulse wave component by subtracting the compensation parameter therefrom.

3. The electronic blood pressure meter as claimed in claim 2, wherein said circumstance in which the pressure in the cuff is outside a range of blood pressure measurement is when the pressure in the cuff is below the range of blood pressure measurement.

4. The electronic blood pressure meter as claimed in claim 2, wherein said circumstance in which the pressure in the cuff is outside a range of blood pressure measurement is when the pressure in the cuff is above the range of blood pressure measurement.

5. An electronic blood pressure meter, comprising:
   (a) a cuff adapted to be fitted around the arm of a patient whose blood pressure is to be measured, said cuff having a cavity;
   (b) means for pressurizing the cavity of said cuff;
   (c) means for gradually depressurizing the cavity of said cuff;

(d) means for sensing the pressure in the cavity of said cuff, and for producing an output signal representative of the pressure in the cavity;
(e) means for detecting a pulse wave component in said output signal produced by the sensing means;
(f) means for determining the amplitude of the pulse wave component detected by said detecting means;
(g) means for determining values for systolic blood pressure and diastlic blood pressure, according to the amplitude of the pulse wave component and according to the output signal produced by the sensing means; and
(h) means for calculating a corrected systolic blood pressure value according to the relationship:

$$SYS = (S - bs)/as$$

where SYS is the corrected systolic blood pressure value, S is the systolic blood pressure value determined by said means for determining vaues for systolic blood pressure and diastolic blood pressure, and bs and as are constants.

6. The electronic blood pressure meter as claimed in claim 5, wherein bs is approximately equal to 11.2 mmHg, and as is approximately equal to 0.91.

7. An electronic blood pressure meter, comprising:
(a) a cuff adapted to be fitted around the arm of a patient whose blood pressure is to be measured, said cuff having a cavity;
(b) means for pressurizing the cavity of said cuff;
(c) means for gradually depressurizing the cavity of said cuff;
(d) means for sensing the pressure in the cavity of said cuff, and for producing an output signal representative of the pressure in the cavity;
(e) means for detecting a pulse wave component in said output signal produced by the sensing means;
(f) means for determining the amplitude of the pulse wave component detected by said detecting means;
(g) means for determining values for systolic blood pressure and diastolic blood pressure, according to the amplitude of the pulse wave component and according to the output signal produced by the sensing means; and
(h) means for calculating a corrected diastolic blood pressure value according to the relationship:

$$DIA = (D - bd)/ad$$

where DIA is the corrected diastolic blood pressure value, D is the diastolic blood pressure value determined by said means for determining values for systolic blood pressure and diastolic blood pressure, and bd and ad are constants.

8. The electronic blood pressure meter as claimed in claim 7, wherein bd is approximately equal to 7.5 mmHg, and ad is approximately equal to 0.91.

* * * * *